United States Patent [19]
Hidalgo et al.

[11] Patent Number: 6,118,526
[45] Date of Patent: Sep. 12, 2000

[54] METHOD FOR MEASUREMENT OF LIGHT TRANSMITTANCE

[75] Inventors: Dennis K. Hidalgo, Lakewood; Kevin L. Gobbo, Golden, both of Colo.

[73] Assignee: Coors Brewing Company, Golden, Colo.

[21] Appl. No.: 08/898,766

[22] Filed: Jul. 23, 1997

Related U.S. Application Data

[63] Continuation-in-part of application No. 08/698,591, Aug. 16, 1996.

[51] Int. Cl.⁷ .................................................. G01N 21/00
[52] U.S. Cl. ......................... 356/239; 356/319; 356/239; 356/240.1; 356/73
[58] Field of Search ............................... 356/239, 240.1, 356/73, 319

[56] References Cited

U.S. PATENT DOCUMENTS

| | | |
|---|---|---|
| 3,387,551 | 6/1968 | Hughes . |
| 3,708,679 | 1/1973 | Stock et al. ........................ 250/223 R |
| 3,767,374 | 10/1973 | Iacovazzi et al. ........................ 65/165 |

(List continued on next page.)

FOREIGN PATENT DOCUMENTS

| | | |
|---|---|---|
| 2 094 530 | 9/1982 | United Kingdom . |
| 2 179 648 | 3/1987 | United Kingdom . |

OTHER PUBLICATIONS

U.S. application No. 08/526,897, Lucas, filed Sep. 12, 1995 for "Hot Bottle Inspection Apparatus and Method".
U.S. application No. 8/831,384, Burns et all., Burns et al. filed date Apr. 1, 1997 for "Hot Bottle Inspection Apparatus and Method".
U.S. application No. 08/898,535, Burns et al., filed Jul. 22, 1997 Hot Bottle Inspection Apparatus.
U.S. application No. 08/914,984, Lucas, filed Aug. 20, 1997 for "Hot Bottle Inspection Apparatus and Method".
U.S. application No. 09/000,808, Lucas filed Dec. 30, 1997 for "Method for Inspecting Translucent Objects Using Imaging Techniques".
U.S. application No. 09/001,215, Lucas, filed Dec. 30, 1997 for "Method for Inspecting Manufactured Articles".
"The Hand Book of Glass Manufacture" vol. II, Fay V. Tooley, published by Books For Industry, Inc. and the Glass Industry Magazine Division of Magazines for Industry, Inc. 1974, Library of Congress No. 74–77520, PPS 961–975.
U.S. application No. 09/181,832, Burns et al., filed Oct. 28, 1998 for "Hot Bottle Inspection Apparatus and Method".

*Primary Examiner*—Frank G. Font
*Assistant Examiner*—Reginald A. Ratliff
*Attorney, Agent, or Firm*—Klaas, Law, O'Meara & Malkin, P.C.; Michael A. Goodwin, Esq.; William P. O'Meara, Esq.

[57] ABSTRACT

An apparatus and method for measuring and analyzing light transmittance through containers is provided. A system is disclosed in which a light probe is insertable into a container in order to measure light transmittance through portions of the container wall. The light probe is connected to a spectrophotometer which analyzes the light transmitted through the container wall. Light transmittance is measured over a series of light wavelengths in order to accurately predict the ability of the container to protect its contents from the detrimental effects of light. In addition, the container may be tested for light transmittance at several locations. The measured light transmittance of each location may be weighted differently in order to compensate for the anticipated exposure to light of the particular location. Also provided is a method for monitoring and controlling a container manufacturing process in which containers may be analyzed for light transmittance and the process adjusted accordingly depending upon the analysis.

27 Claims, 13 Drawing Sheets

U.S. PATENT DOCUMENTS

| | | | |
|---|---|---|---|
| 3,886,356 | 5/1975 | Gomm et al. | 250/223 |
| 4,004,904 | 1/1977 | Fergusson | 65/158 |
| 4,019,819 | 4/1977 | Lodzinski | 356/73 |
| 4,026,656 | 5/1977 | Kusz et al. | 356/51 |
| 4,306,835 | 12/1981 | Hurley | 415/118 |
| 4,332,606 | 6/1982 | Gardner | 65/158 |
| 4,402,721 | 9/1983 | Ericson et al. | 65/29 |
| 4,431,436 | 2/1984 | Lulejian | 65/159 |
| 4,492,476 | 1/1985 | Miyazawa | 356/428 |
| 4,494,656 | 1/1985 | Shay et al. | 209/524 |
| 4,500,203 | 2/1985 | Bieringer | 356/240 |
| 4,553,217 | 11/1985 | Daudt et al. | 364/560 |
| 4,599,099 | 7/1986 | Jones | 65/29 |
| 4,606,746 | 8/1986 | Keller | 65/29 |
| 4,608,072 | 8/1986 | Fenton | 65/79 |
| 4,614,531 | 9/1986 | Bishop et al. | 65/158 |
| 4,639,263 | 1/1987 | Kulikauskas | 65/158 |
| 4,649,503 | 3/1987 | Keller | 364/552 |
| 4,664,521 | 5/1987 | Scott et al. | 356/240 |
| 4,675,042 | 6/1987 | Taddei-Contreras et al. | 65/158 |
| 4,679,075 | 7/1987 | Williams et al. | 358/106 |
| 4,691,830 | 9/1987 | Ahl et al. | 209/523 |
| 4,694,158 | 9/1987 | Leser | 250/223 |
| 4,762,544 | 8/1988 | Davey | 65/29 |
| 4,915,237 | 4/1990 | Chang et al. | 209/524 |
| 4,948,956 | 8/1990 | Fukuchi | 250/223 |
| 4,997,769 | 3/1991 | Lundsgaard | 436/66 |
| 5,187,368 | 2/1993 | Galante et al. | 250/341 |
| 5,305,081 | 4/1994 | Gooch et al. | 356/239.4 |
| 5,345,309 | 9/1994 | Wertz et al. | 356/372 |
| 5,437,702 | 8/1995 | Burns et al. | 65/29.12 |
| 5,510,610 | 4/1996 | Baldwin | 250/223 B |
| 5,510,621 | 4/1996 | Goldman | 250/343 |
| 5,717,486 | 2/1998 | Burri et al. | 356/240 |
| 5,734,467 | 3/1998 | Lucas | 356/240.1 |

METHOD FOR MEASUREMENT OF LIGHT TRANSMITTANCE

This is a continuation-in-part of application Ser. No. 08/698,591 filed Aug. 16, 1996, which is hereby incorporated by reference for all that is disclosed therein.

FIELD OF THE INVENTION

The present invention relates generally to a method and apparatus for measuring light transmittance through translucent materials and, more particularly, to a method and apparatus for measuring light transmittance through portions of beverage containers.

BACKGROUND OF THE INVENTION

Beverages are commonly packaged in containers which are made from translucent materials. Examples of such materials include glass and plastic. Because they are formed of translucent materials, such containers do not completely block light from passing through the container wall. Accordingly, the contents of a translucent container may be exposed to light from outside of the container.

The taste of some beverages may be detrimentally affected by light. In beer, for example, exposure to light causes a breakdown of certain sulfur compounds existing in the beer. The presence of these sulfur compounds is due to the addition of hops, an ingredient of beer. The products of this breakdown result in an undesirable flavor profile in the beer which is detectable by both taste and smell. This flavor profile is commonly referred to in the beer brewing industry as "light-struck flavor" and is often described as having a "skunky" flavor and odor.

It has been found that some wavelengths of light, more than others, induce light struck flavor in beer. FIG. 1 graphically illustrates the amount of light struck flavor induced in beer versus light wavelength. As can be seen, wavelengths of light of up to about 550 nm have the greatest impact on light struck flavor in beer. Wavelengths of light above about 550 nm, on the other hand, have little effect.

Because of the light-struck flavor problem, it is desirable to reduce or eliminate the exposure of beer to light in the wavelength range described above. This represents a particular challenge when beer is packaged in translucent containers. The ability of a translucent material to block the transmission of light depends upon both the thickness and the color of the material used. The most common translucent containers used for packaging beer are glass bottles.

The manufacture of glass bottles begins with the preparation of raw materials. A batch of raw materials is formed by measuring sand, soda ash and other ingredients in precise quantities and then mixing them together. The batch is then conveyed to storage silos located over large melting furnaces. The mixed batch materials are continuously metered into furnaces to replace molten glass which is dispensed from the furnaces after melting.

The furnaces are heated by a combination of natural gas and electricity and are operated at a temperature of over 2500 degrees Fahrenheit. The melted mixture of raw materials forms molten glass which flows from the furnaces through refractory channels, also known as forehearths, to a position over bottle forming machines.

A bottle forming machine known in the industry as an "I.S. machine" draws the glass into individual gobs and drops each gob into a blank mold. The blank mold forms a bottle preform, also referred to as a parison. The preform is transferred to a blow mold where it is blown by compressed air into a bottle.

An I.S. machine typically has between six and sixteen individual sections, with each section having from one to four blow mold cavities. Each section may be capable of manufacturing one to four bottles at a time. A typical eight section, triple gob, I.S. machine used in the production of beer bottles may produce 270 beer bottles per minute.

After the bottles have been blown, they are transferred from the respective blow mold cavities onto a moving conveyor belt. The finished bottles transferred onto the conveyor from the blow mold are still red hot (approximately 1,000 degrees Fahrenheit). These hot bottles are conveyed by the conveyor belt through a hot end coating hood where they are chemically treated with a stannous chloride compound for strengthening.

After passing through the hot end coating hood, the hot bottles are conveyed through an annealing oven or lehr where they are reheated and then cooled in a controlled manner to eliminate stresses in the glass. The annealing process is the last process which takes place at the hot end of the production line. The portion of the production line downstream from the annealing oven is referred to as the "cold end" of the production line. At the cold end of the production line, bottles are conveyed through a series of inspection devices.

After passing through the cold end inspection stations, bottles are transferred to a case packer machine, placed into a cardboard carton and conveyed to a palletizer machine for being placed in pallets. Loaded pallets are then shipped to a filling facility, such as a brewery.

In order to provide effective light-blocking properties in glass containers, such as glass bottles, amber colored glass is generally used to form the bottles. When making amber colored glass bottles, iron-bearing minerals such as pyrite or melite and graphite are generally added to the batch in precise quantities. The color of the finished glass depends upon the specific chemistry of the glass batch which can itself vary due to, e.g., variations in the raw material used. Often, previously manufactured glass bottles are crushed and added to the batch. Because crushed glass, commonly referred to in the industry as "cullet", varies in composition, its addition also causes variations in the feed stock for the glass and may, thus, impact the color and quality of the final glass produced.

Accordingly, it is desirable to regularly perform quality control checks on glass bottles to ensure that they are capable of adequately blocking light. Normally, to accomplish such checks, samples of bottles are removed from the glass production line for testing. One object of this testing is to detect glass batch material variations which allow an unacceptable amount of light to be transmitted through the bottle. Another object of such testing is to test new bottle designs which may have different wall thicknesses than previously used designs.

One such test that is commonly performed is a flavor panel test. In this type of test, bottle samples are first filled with beer. The bottles are then exposed to a predetermined level of light for an extended time period. This time period may be, for example, 14 days or longer.

After exposure to light for the requisite time period, the beer in the bottles is tasted by members of a trained beer tasting panel. The panel members then determine if any light struck flavor exists in the beer, and the bottles are then accepted or rejected as appropriate.

One problem with the flavor panel test is the relatively large amount of time which elapses between bottle manufacture and the results of the test. During the several day period required for the test, tens of thousands of bottles may be produced. Accordingly, if a problem is detected by the flavor panel test, all of bottles produced during the testing period may have to be destroyed. This time delay may represent a particular problem when a new bottle design is being introduced.

Because of this time delay problem, efforts have been made to analyze bottle samples shortly after they are produced to predict whether the bottles will pass the flavor panel test. The traditional method used to accomplish this analysis is a destructive test in which a portion is first cut out of the bottle wall. This portion may measure approximately 1 cm by 5 cm and may be cut from the label panel portion of the bottle. The cut portion is then placed into a spectrometer and the transmittance of light through the portion is then measured at a particular wavelength of light. Typically, the thickness of the cut portion is also measured and the measured transmittance is then standardized back to a standard glass thickness, e.g., ⅛ inch thick glass. As can be appreciated, this procedure focuses only on the color density of the glass, and not its overall ability to block light transmittance.

If the procedure indicates that the glass is defective, then changes can immediately be made to the process or bottle design, or both, to correct the problem and the time delay associated with the flavor panel test can be avoided. If, on the other hand, the procedure indicates that the glass is acceptable, then the production of glass bottles can continue with the expectation that the flavor panel test will also be favorable.

The destructive test described above is intended to solve the time-delay problem associated with the flavor panel test. In reality, however, it has been found that the destructive test often fails to accurately detect defective bottles which are subsequently rejected by the flavor panel test. In other words, the flavor panel test often rejects samples of particular glass batches or bottle designs that had previously been indicated as acceptable by the destructive test.

Such failures by the destructive test often occur because, as described above, only color density is analyzed and because light of only a single wavelength is measured. The traditional destructive test measures light transmittance only at around 550 nm. As previously described, however, light struck flavor in beer is induced by a range of light wavelengths of up to about 550 rim.

FIG. 2 graphically illustrates an example of glass which is well suited for preventing light struck flavor in beer. As can be appreciated, the glass illustrated in FIG. 2 allows the passage of very little light in the light struck flavor wavelength range of less than 550 nm.

FIG. 3 graphically illustrates a glass sample which exhibits relatively low, e.g., about 3%, transmittance at 550 nm, but which exhibits relatively high transmittance over the majority of the light-struck flavor inducing range. Glass exhibiting these characteristics might pass the destructive test, previously described, because the destructive test only analyzes light transmittance at 550 nm. Since a large amount of light in the light-struck flavor inducing range is unblocked by the glass, however, light struck flavor might very well be induced and a bottle made from such glass would, therefore, most likely fail the flavor panel test.

In addition to the problem described above, the destructive test also has the disadvantage of being slow. A typical test using the destructive testing method outlined above, may take approximately two hours.

Because the destructive test entails cutting portions out of bottles, it requires manual labor and, accordingly, is not conducive to automation. Finally, the destructive test, as its name indicates, requires destruction of the bottle being tested. Accordingly, bottles tested by this method cannot later be used for packaging beer or other beverages.

Thus, it would be generally desirable to provide an apparatus and method which overcomes these problems associated with the testing of beverage containers for light transmittance.

SUMMARY OF THE INVENTION

The present invention is directed to a method for inspecting containers in which a probe is inserted into the open end of the container. The probe is attached to a spectrometer. Light provided by a light source located outside of the container is transmitted through the container wall and onto the probe. In this manner, the spectrophotometer attached to the probe can measure the light transmittance through the material forming the container. Thus, containers may be tested for light transmittance in a non-destructive fashion which is also conducive to automation.

While testing, the probe may be moved to several locations relative to the container by inducing relative axial and rotational movement between the probe and the container. In this manner, light transmittance data readings from several different portions of the container may be obtained. When analyzing this data, the readings may be weighted differently depending upon the amount of light to which the particular portion of the container is likely to be exposed. This data may also be used to analyze the glass distribution within the container.

The invention is also directed to a method of measuring the light transmittance of a material for use in a beer container. The light transmittance is measured over a range which substantially corresponds to the range of light frequencies which induce light struck flavor in beer. Accordingly, the method is capable of accurately predicting the ability of a particular container material to prevent beer packaged therein from acquiring light struck flavor.

The invention is also directed to a method for monitoring and controlling a container manufacturing process. According to this aspect of the invention, a statistical sampling of containers may be removed from a conveyor downstream of the container manufacturing machine. The removed containers may then be analyzed for light transmittance and the results compared with those associated with a control container. If a variance in light transmittance is detected, the thickness of the container may be measured in order to determine whether the light transmittance variance is being caused by a variance in container thickness or a variance in container composition or both. Alternatively, a control piece of predetermined thickness may be constructed. After the light transmittance of the control piece is measured, the light transmittance measurement and the thickness of the control piece may be used to calculate a container material composition constant. This constant, in turn, may be used to calculate the thickness of the sample bottles based upon the measured light transmittance of the sample bottles. If the material composition constant varies from an acceptable range, then the composition of the container material batch may be adjusted accordingly. If, on the other hand, the thickness of the containers varies from an acceptable range, then the tooling used to form the containers may be adjusted.

DETAILED DESCRIPTION OF THE INVENTION

Figure 1:
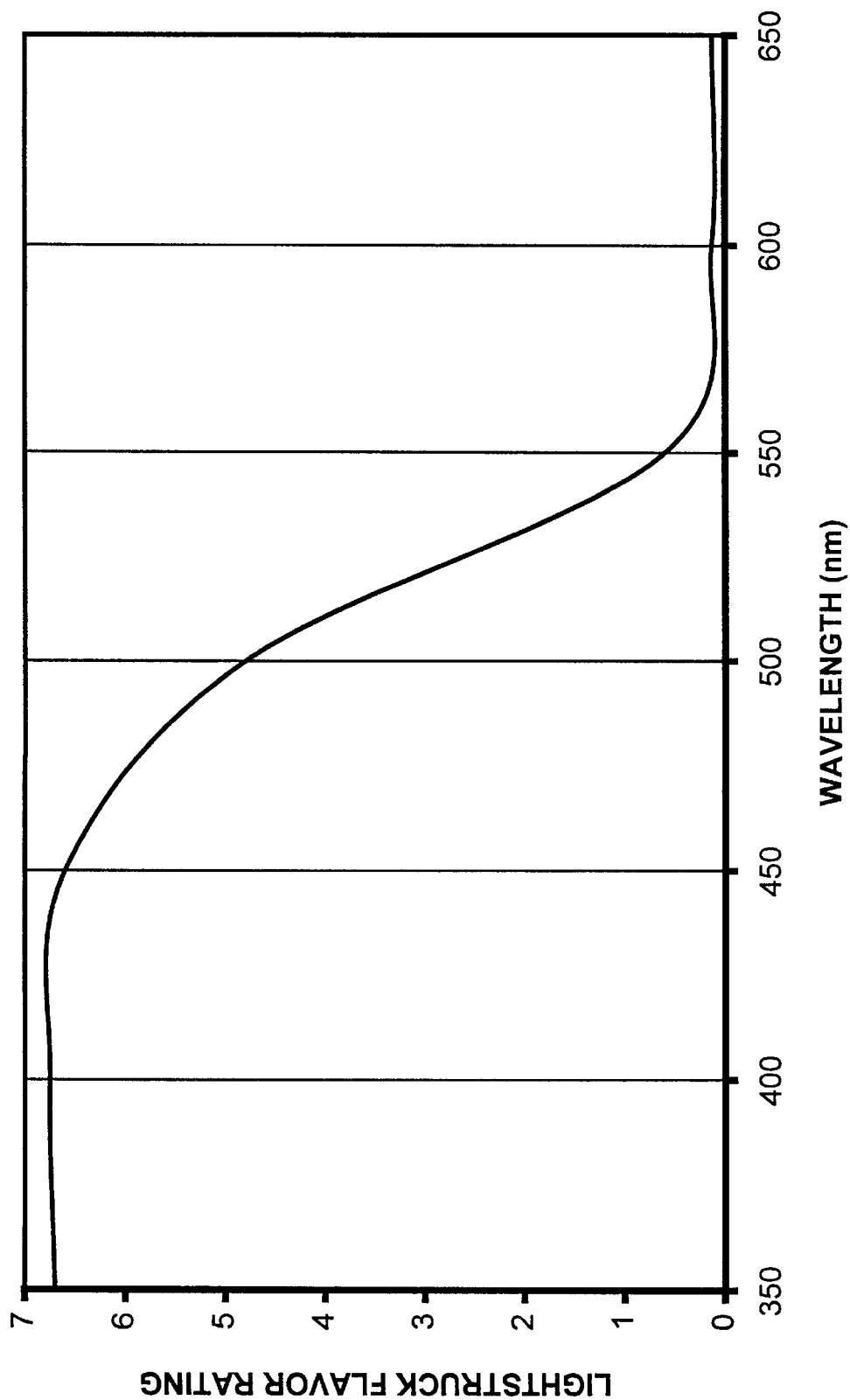
FIG. 1 is a graph illustrating light struck flavor rating in beer versus wavelength of light.

In general, the invention may pertain to a method of monitoring a process 500 for forming a plurality of translucent containers 510. The method may include the steps of making a measurement of light transmittance through a first portion 148 of a wall member of at least one sample container 520 of the plurality of containers 510; making a comparison of the measurement to a predetermined acceptable level of light transmittance; and determining whether the process 500 is in need of adjustment based upon the comparison. The first portion 148 of the wall member of the sample container 520 is an integral part of the sample container 520 during the step of making the measurement of light transmittance.

The invention may also pertain generally to a method of monitoring a process 500 for forming a plurality of translucent containers 510. The method may include the steps of making a measurement of light transmittance through a first portion 148 of a wall member of at least one sample container 520 of the plurality of containers 510; making a comparison of the measurement to a predetermined acceptable level of light transmittance; and determining whether the process 500 is in need of adjustment based upon the comparison. The light intensity reading comprises a set of light intensity readings across a range of light frequencies.

The invention may also pertain generally to a method of measuring the transmittance of light through a wall of a container 140 using a light source 60 and a spectrophotometer 72 having an associated probe 120. The method may include the steps of positioning the container 140 so that the spectrophotometer probe 120 is at least partially located within the container 140 and a first portion 156 of the wall of the container 140 is located between the light source 60 and the probe 120; supplying light from the light source 60 onto the spectrophotometer probe 120 through the first portion 156; using the spectrophotometer 72 to generate at least a first light intensity reading in response to the light supplied through the first portion 156 of the wall of the container 140; and using the at least a first light intensity reading to determine a percent transmittance of light through the wall of the container 140.

Having thus described the light transmittance method in general, further features thereof will now be specifically described.

Testing System

Figure 4:
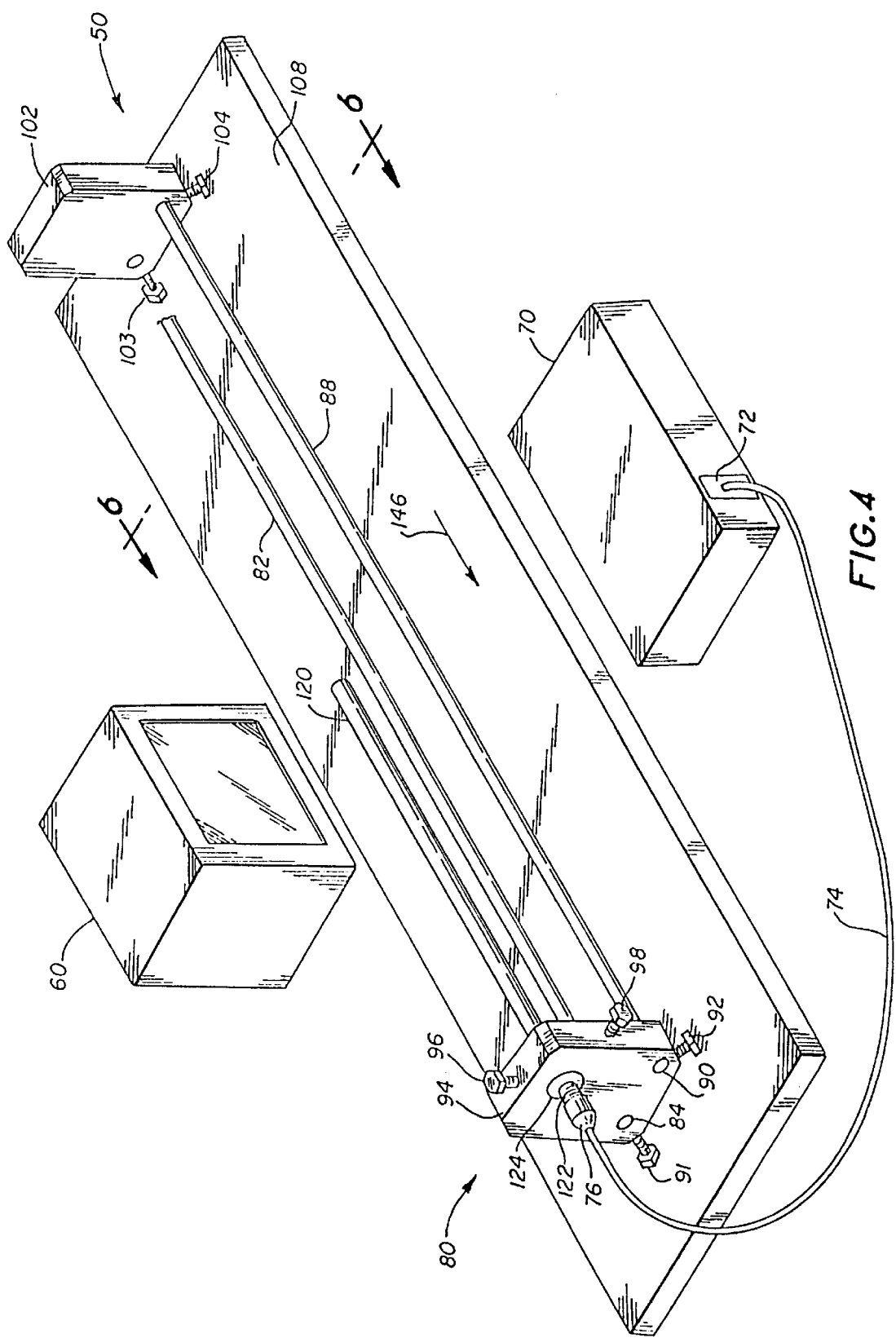
FIG. 4 is a top perspective view of a container light transmittance testing apparatus.

FIG. 4 shows a container testing system 50 which generally includes a light source 60, a computer 70 and a container support apparatus 80. As will be explained in more detail herein, during operation of the container testing system 50, light from the light source 60 is passed through a portion of the wall of a container, such as the bottle 140, FIG. 8, and onto the probe 120 of the container support apparatus 80. The light is then transmitted via fiber optic cable 74 to a spectrophotometer card 72 located within computer 70 for analysis.

Light source 60 may be a xenon light source and may, for example, be of the type commercially available from Dolan Jenner Company of Lawrence, Mass. and sold as a "Xenon 175 Fiber-Lite".

It has been found that a xenon light source is ideal for measuring light transmittance through containers because a xenon light source provides relatively high light energy over the entire light wavelength range of 400 to 550 nm as will be discussed in further detail herein. It is noted, however, that other types of light sources, such as a quartz halogen light source, may alternatively be used with satisfactory results.

Container support apparatus 80 may include a pair of container support rails 82, 88. The support rails 82, 88 may be supported at each end thereof within support blocks 94 and 102. With reference to the support block 94, for example, it can be seen that the support rails 82, 88 may pass through openings in the support block 94, terminating at end portions 84, 90, respectively. The support rails 82, 88 may be held in place within the support block 94 by set screws 91 and 92 respectively.

In a similar manner, the support rails 82, 88 may be held in place within the support block 102 by set screws 103 and 104, respectively. Alternatively, the support rails 82, 88 may be held in place within the respective support blocks 94, 102 by press-fitting the rails 82, 88 within the support blocks or they may be attached in any other conventional manner.

The rails 82, 88 may be formed of metal or of any other relatively rigid material and may each have a length of about 440 mm between the support blocks 94, 102. Each rail 82, 88 may have a diameter of about 6.0 mm. Although illustrated as round, it is to be understood that the rails 82, 88 may be of any shape which is conducive to supporting a container as will be explained in further detail herein.

Figure 7:
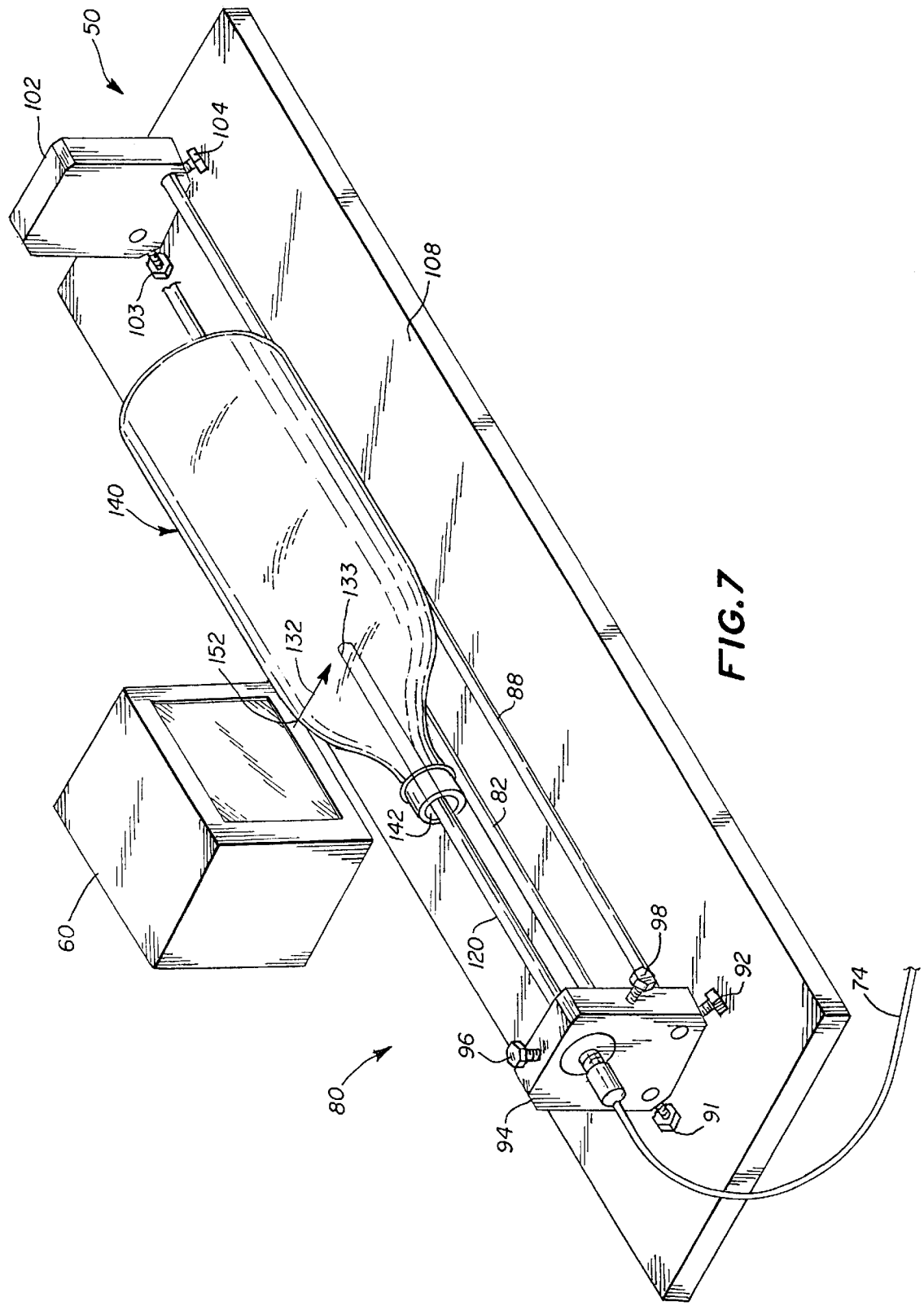
FIG. 7 is a top perspective view of the testing apparatus of FIG. 4 with a container installed.

A probe 120 may be mounted to the support block 94 in a cantilevered fashion as shown in FIG. 4. Probe 120 may, for example pass through a hole in the support block 94 and terminate in a threaded end 122. Probe threaded end 122 may, in turn, be engaged by a threaded nut 124, as shown, in order to securely fasten the probe 120 to the support block 94. The probe 120 may also be mounted to the support block 94 by set screws 96, 98 as shown in FIGS. 4 and 7. Alternatively, probe 120 may be mounted within support block 94 in any conventional manner.

Support blocks 94, 102 may be mounted to a support apparatus base member 108 by screws or bolts, not shown, or by any conventional mounting mechanism. It is noted that, although the container support apparatus 80 has been described herein as having a fixed relationship between its components, it could, alternatively, be constructed in an adjustable manner in order to easily facilitate testing of bottles of different sizes and shapes.

Figure 5:
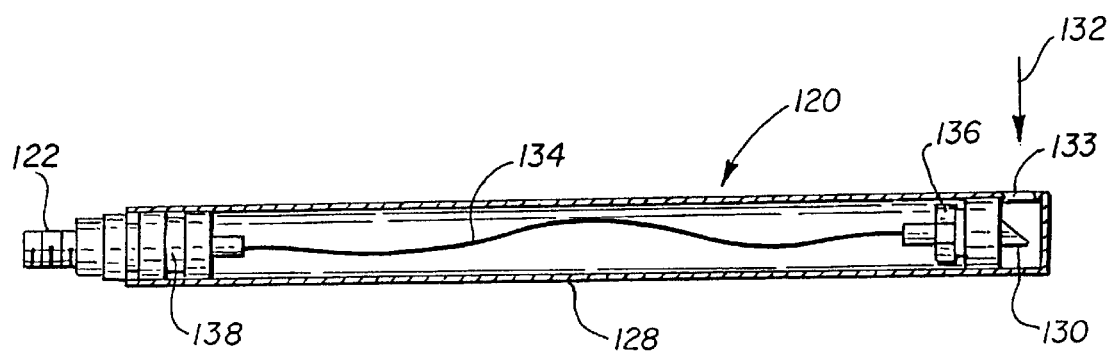
FIG. 5 is a top cross section view of a probe used in the testing apparatus of FIG. 4.

FIG. 5 shows a top cut-away detail view of the probe 120. As can be seen, probe 120 may comprise a generally cylindrical housing portion 128. Located within the housing portion 128 is a prism assembly 130 which may be oriented to receive light generated by light source 60 from a direction 132 as shown, FIG. 7. The probe housing portion 128 may be provided with a window 133 in the area adjacent the prism 130 in order to allow light to reach the prism 130 as described above. The prism of prism assembly 130 reflects the received light 90 degrees, in a conventional manner, in order to direct the light into a fiber optic cable 134 located within probe housing 128. Fiber optic cable 134 may be attached to the prism assembly 130 via a coupling member 136 in a conventional manner. Fiber optic cable 134 may be connected to the previously described probe threaded end 122 via a second coupling 138, also in a conventional manner. In this manner, light from the light source 60 may be reflected by the prism 130 and directed along the fiber optic cable 134 to its terminal end which is located at the end of probe threaded end 122. When cable 74, FIG. 4, is attached to probe threaded end 122, as previously described, the light may be further transmitted along the cable 74 and to the spectrophotometer card 72 housed in computer 70.

The probe 120 may have a length of about 193 mm outside of the support block 94. Probe 120 may have a diameter of about 12.0 mm. Although illustrated as round, it is to be understood that the probe 120 may be of any shape which is conducive to its operation, as will be explained in further detail herein.

Figure 6:
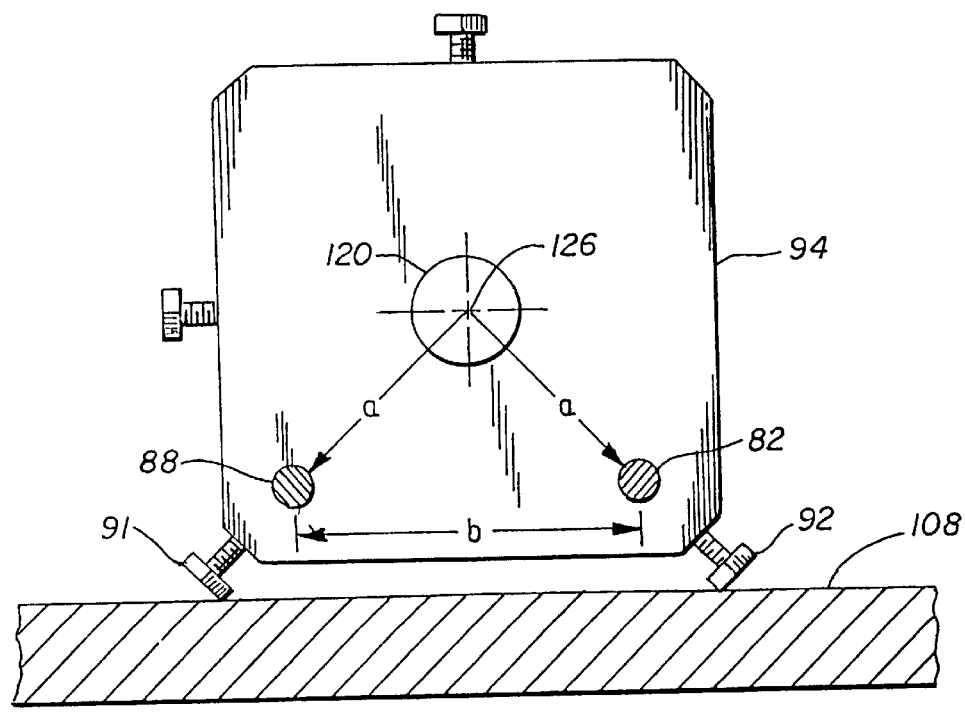
FIG. 6 is a cross section view of the testing apparatus of FIG. 4 taken along the line 6—6 of FIG. 4.

As shown in FIG. 7, the container support apparatus 80 may be designed to support a container such as the bottle 140 so that the probe 120 is centered within the bottle opening 142. To accomplish this, the bottle 140 may be supported on its outer circumference by the container support rails 82 and 88 as shown. FIG. 6 illustrates a cross-section view taken along the line 6—6 of FIG. 4. As can be appreciated from FIG. 6, the center 126 of the probe 120 is located a distance "a" from outer circumferential surface of each of the support rails 82 and 88. In order to ensure that the probe 120 will be aligned with the opening of a container to be tested, the distance "a" should be chosen to coincide with the size of the radius of the container at its outer surface, or one-half its diameter "d", FIG. 8. The distance "b" between the centers of the rails 82, 88 should be chosen to be less than the diameter "d" of the container to be tested. In one example, in which a container having an outside radius of about 30.5 mm (and an outside diameter "d" of about 61 mm) is to be tested, the distance "a" may be made to equal approximately 30.5 mm. The distance "b" may be about 30.0 mm.

Referring again to FIG. 4, computer 70 may be a conventional personal computer such as a personal computer utilizing a 486/66 processor chip manufactured by Intel Corporation. A spectrophotometer card 72 may be inserted into the computer 70. Spectrophotometer card 72 may have a sampling range of 375 nm to 720 nm and a resolution of 2 nm and may be of the type commercially available from Control Development Inc. Of South Bend Ind. and sold as part number CDIOSC/375-720/2.0. A fiber optic cable 74 may be attached to the spectrophotometer card 72 at one end and terminate in a connector 76 at its other end. The connector 76 may be operatively connected to the probe 120 in a conventional manner as shown in FIG. 4.

Percent Light Transmittance Testing Procedure

Figure 8:
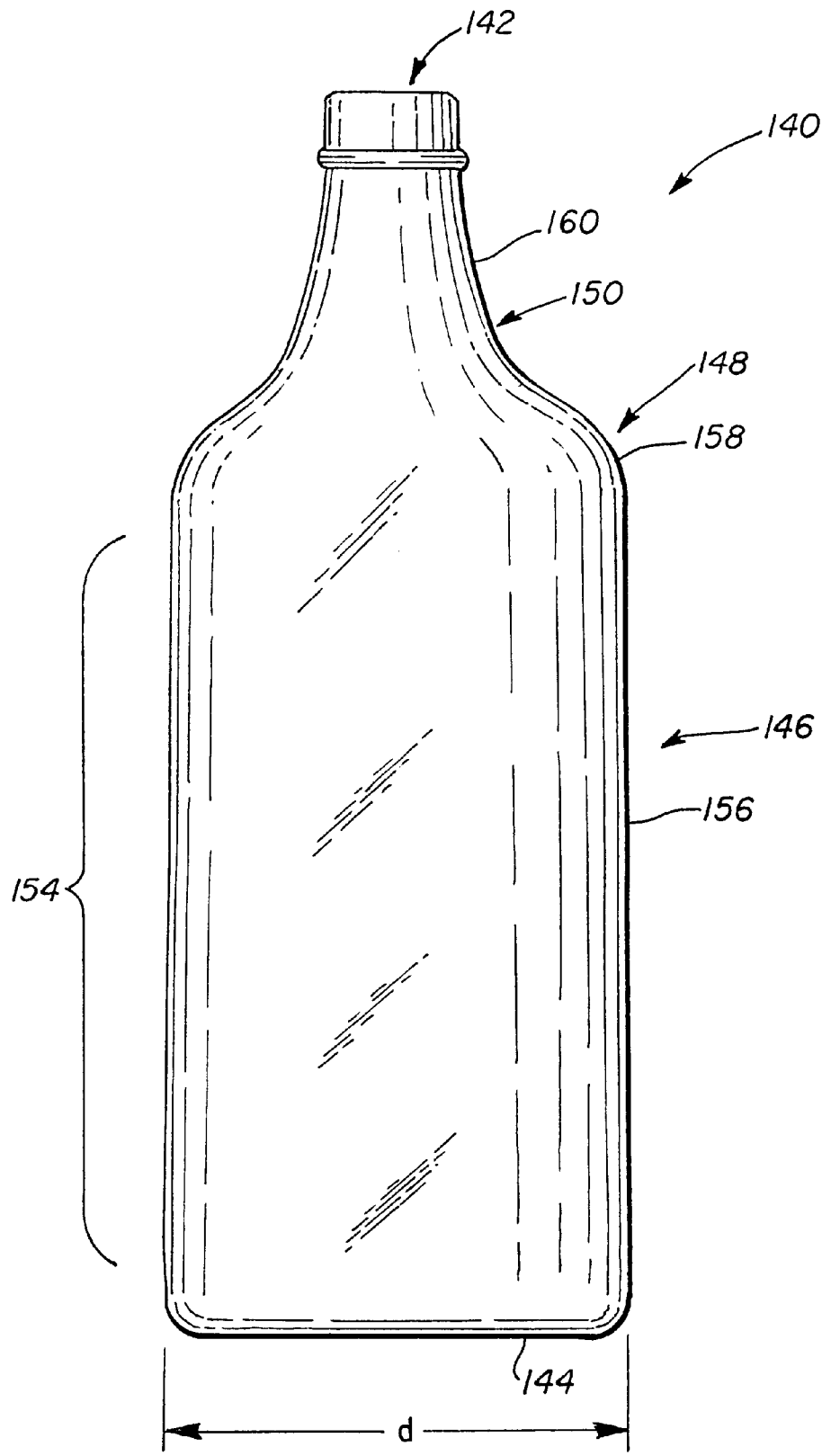
FIG. 8 is an elevation view of an exemplary container.

A procedure for measuring the transmittance of light through the wall of a container will now be described in detail. FIG. 8 schematically illustrates a conventional bottle 140 of the type which might typically be tested with the container testing system 50. Bottle 140 has a base 144 and an oppositely disposed open end 142 which may comprise a threaded open end to facilitate attachment and removal of a bottle closure or "crown" in a conventional manner after the bottle 140 is filled. Located generally between base 144 and open end 142 may be a sidewall portion 146, a shoulder portion 148 and a neck portion 150. The bottle 140 may have an overall height, from base 144 to open end 142 of about 194 mm and a diameter "d" of about 61 mm.

FIG. 7 shows a container, such as the bottle 140 mounted on the container support apparatus 80. To mount the bottle in this manner, the bottle 140 may first be placed on the container support apparatus support rails 82, 88 with its open end 142 facing the support block 94 and its base 144, FIG. 8, proximate the support block 102. The bottle may then be slid along the rails 82, 88, in the direction of the arrow 146 in FIG. 4, until the bottle reaches the position shown in FIG. 7 with the probe 120 entering the bottle 140 through bottle open end 142.

As an initial step in testing a container, such as the bottle 140, the container testing system 50 may be calibrated by activating the light source 60 before the bottle 140 is placed on the container support apparatus 80. With no container located on the container support apparatus 80, light from light source 60 will impinge directly upon the probe prism 130 and subsequently be transmitted along probe fiber optic cable 134 and cable 74 to the spectrophotometer 72 housed within the computer 70. The spectrophotometer may then be used to obtain a series of light intensity readings across the desired spectrum of light wavelengths. As can be appreciated, these calibration readings correspond to light which directly impinges upon the probe 120 without first passing through a container wall.

After calibration, a container light transmittance measurement may be made as follows. First, a container, such as the bottle 140, may be mounted on the container support apparatus 80 as previously described. With the bottle 140 mounted in this manner, a portion 152, FIG. 7, of the bottle sidewall 146, will be located between the probe window 133 and the light source 60. Light from light source 60 will, thus pass in direction 132 through the bottle sidewall portion 152 and then impinge upon the probe prism 130 and subsequently be transmitted along probe fiber optic cable 134 and cable 74 to the spectrophotometer 72 housed within the computer 70. The light which reaches the spectrophotometer 72 when a container is in place, as described above, is thus indirect light, the intensity of which is reduced according to the light blocking characteristics of the container portion 152. The spectrophotometer may then be used to obtain a series of light intensity readings of this indirect light across the desired spectrum of light wavelengths.

The container indirect light intensity readings may be compared to the calibration direct light intensity readings for each light wavelength which was sampled. As can be appreciated, the indirect light intensity readings will always be less than the direct calibration light intensity readings because the indirect readings are obtained when container portion 152 is located between the light source 60 and the probe 120. The ability of the container portion 152 to transmit light may be expressed as the ratio of the indirect light intensity for portion 152 to the direct light intensity at a particular wavelength of light. Specifically, the percentage light transmittance for a particular wavelength of light may be calculated as follows:

$$\text{percent transmittance} = \frac{100 \times ILI}{DLI}$$

where ILI=the indirect light intensity measured through container portion 152 at a particular wavelength of light and DLI=the direct transmittance measured at the same wavelength of light during the calibration step. When the percent transmittance is calculated for a series of light intensity readings over a range of light wavelengths, as described below, a graph, such as the graph shown in FIG. 2 may be generated by plotting percent transmittance versus light wavelength. In this manner, the profile of a container's ability to block light over a range of light wavelengths may be obtained.

Container Area Weighted Average Measurement & Calculation

In order to accurately predict the ability of a particular container to protect its contents, e.g., beer, from the detrimental effects of light, it may be desirable to measure the light transmittance at a plurality of points on the container, rather than simply at a single point 152 as described above. It has been found that some areas of a container are naturally exposed to more light and, therefore, have the potential to transmit more light. Referring to FIG. 8, for example, the bottle shoulder area 148 is generally exposed to a relatively high amount of light. Although filled containers, such as the bottle 140, are often shipped and stored in cardboard six-pack carriers or other secondary packaging devices, the shoulder portion 148 usually extends above the walls of such six-pack carriers and is, thus, exposed to ambient light. In addition, because the shoulder area 148 is more horizontal than other portions of the bottle, it may be more directly exposed to overhead ambient lighting which is often prevalent.

In contrast to the shoulder area 148, the sidewall area 146 of bottle 140 is generally exposed to a relatively small amount of light. As previously described, containers, such as the bottle 140, are often shipped and stored in cardboard six-pack carriers or other secondary packaging devices. The location of sidewall area 146 is such that it is generally shielded by the six-pack carrier when the bottle is housed in such a carrier. In addition, the sidewall area 146 comprises a substantially vertical surface and, thus, is not directly exposed to overhead ambient lighting. Sidewall area 146 may also be, at least partially, shielded from light by the presence of a container label. Such labels are generally affixed to the bottle 140 in a "label panel" area 154 which is located within the sidewall area 146 as shown in FIG. 8. Although such labels do not ordinarily wrap completely around the circumference of the bottle, they nevertheless block a substantial amount of light from entering the bottle 140 through the sidewall area 146.

Neck area 150, like shoulder area 148, will extend above the walls of a six-pack carrier and, thus, is exposed to substantially more light than the sidewall area 146. Like sidewall area 146, however, neck area 150 is usually substantially vertical and, thus not directly exposed to overhead ambient light. In addition, neck area 150 is often provided with a neck label which partially blocks light which would otherwise be transmitted through the neck area 150. Accordingly, the neck area 150 will generally be exposed to more light than the sidewall area 146, but less light than the shoulder area 148.

As described above, different areas of the bottle 140 may be exposed to varying levels of light during normal shipment, storage and display. Accordingly, light transmittance measurements from these areas may be weighted according to the anticipated level of exposure to light of each area. A light transmittance reading from neck area 150, for example, might be weighted more heavily than a light transmittance reading from sidewall area 146. In a similar manner, a light transmittance reading from shoulder area 148 might be weighted more heavily than a reading from the neck area 150.

Figure 9A:
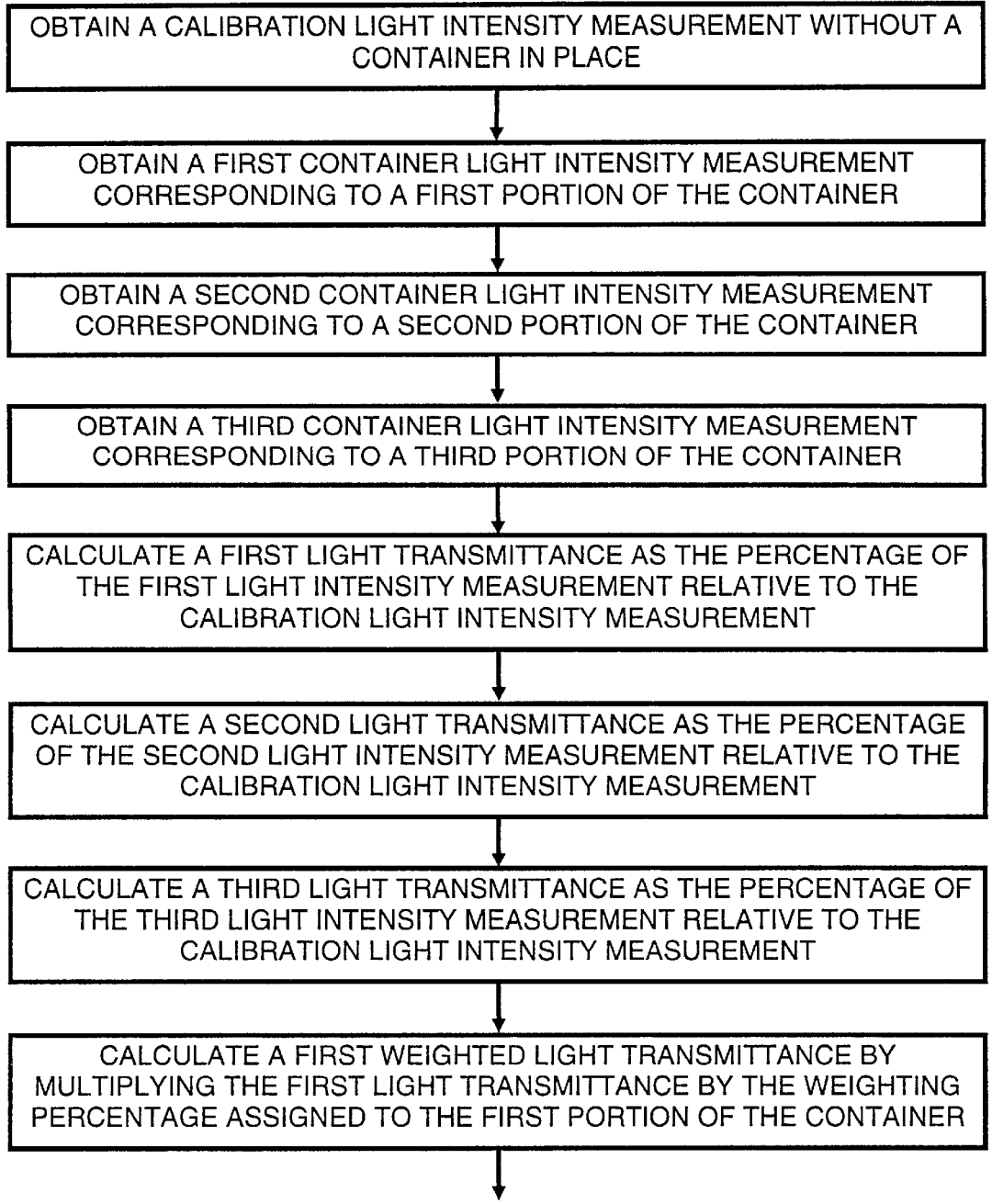
FIGS. 9A and 9B are a flowchart illustrating a method for arriving at the weighted average light transmittance of a container.
Figure 9B:
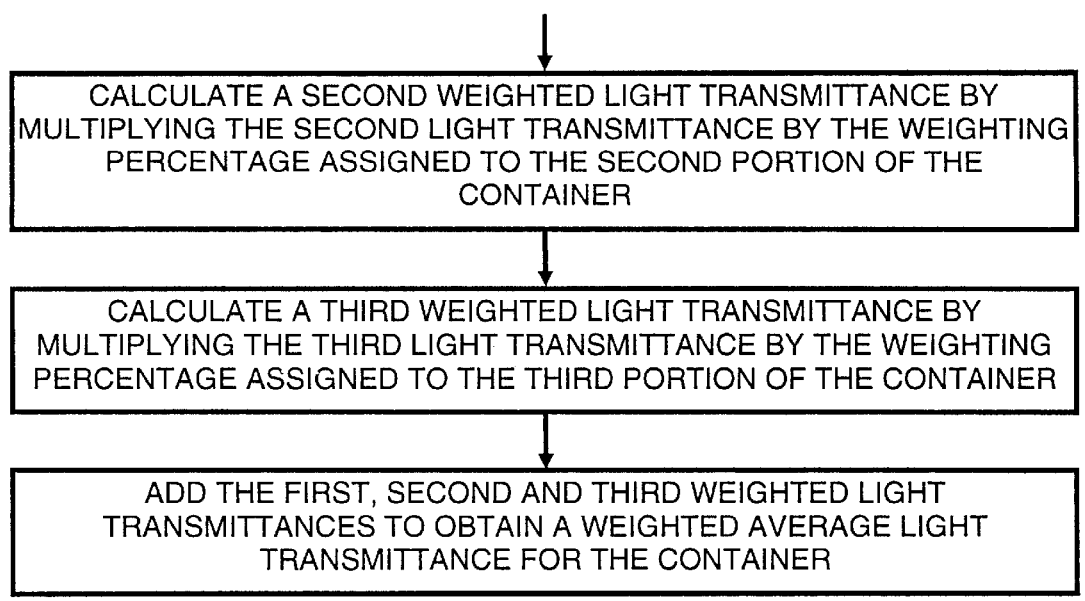

An example of such a weighting procedure will now be explained with reference to the three bottle areas previously described. This weighting procedure is also illustrated in flowchart form in FIG. 9. First, a sidewall area 146 light transmittance reading may be obtained by positioning the bottle 140 on the container support apparatus 80 such that a bottle portion, such as the portion 156, FIG. 8, is located between the light source 60 and the probe window 133. A sidewall area percent light transmittance may then be obtained by measuring the percent light transmittance of the portion 156, in a manner as previously described, over a range of light wavelengths.

A second, shoulder area 148, light transmittance reading may next be obtained. To accomplish this, the bottle 140 may be slid along the container support apparatus rails 82, 88 in a direction toward the support block 102, FIG. 7, until bottle portion 158, FIG. 8, is located between the light source 60 and the probe window 133. A shoulder area percent light transmittance may then be obtained by measuring the percent light transmittance of the portion 158, in a manner as previously described, over a range of light wavelengths.

Finally, a third, neck area 150, light transmittance reading may be obtained. To accomplish this, the bottle 140 may be slid further along the container support apparatus rails 82, 88 in a direction toward the support block 102, FIG. 7, until bottle portion 160, FIG. 8, is located between the light source 60 and the probe window 133. A shoulder area percent light transmittance may then be obtained by measuring the percent light transmittance of the portion 160, in a manner as previously described, over a range of light wavelengths.

After obtaining the three percent light transmittance readings as described above, each reading may be weighted as follows. Because the bottle sidewall area 146 is exposed to the least amount of light, it may be relatively lightly weighted at, for example, 20 percent. Because the shoulder area 148 is exposed to the least amount of light, it may be relatively heavily weighted at, for example, 50 percent. The neck area 150, which receives an intermediate amount of light, may be given an intermediate weight of, for example, 30 percent.

To obtain a weighted average light transmittance for the entire bottle 140, the light percent transmittance, as described previously, measured from each area may be multiplied by the weighting percentage described above. The products of these multiplications may then be added to obtain a weighted average light transmittance for the entire container. Specifically, using the example percentages outlined above, the sidewall percent light transmittance, measured at the bottle portion 156, is multiplied by 20 percent.

The shoulder area percent transmittance, measured at the bottle portion 158, is multiplied by 50 percent. The neck area percent transmittance, measured at the bottle portion 160, is multiplied by 30 percent. These three products may then be added to arrive at a weighted percent light transmittance for the entire container. It is to be understood that, if the light transmittance is measured at a plurality of light wavelengths, as previously described, then the weighting calculation described above may be carried out for each wavelength of light for which data was acquired. This weighted percent light transmittance may then be compared to a predetermined acceptable level to determine whether the tested container is likely to adequately protect the container contents from light.

Figure 10:
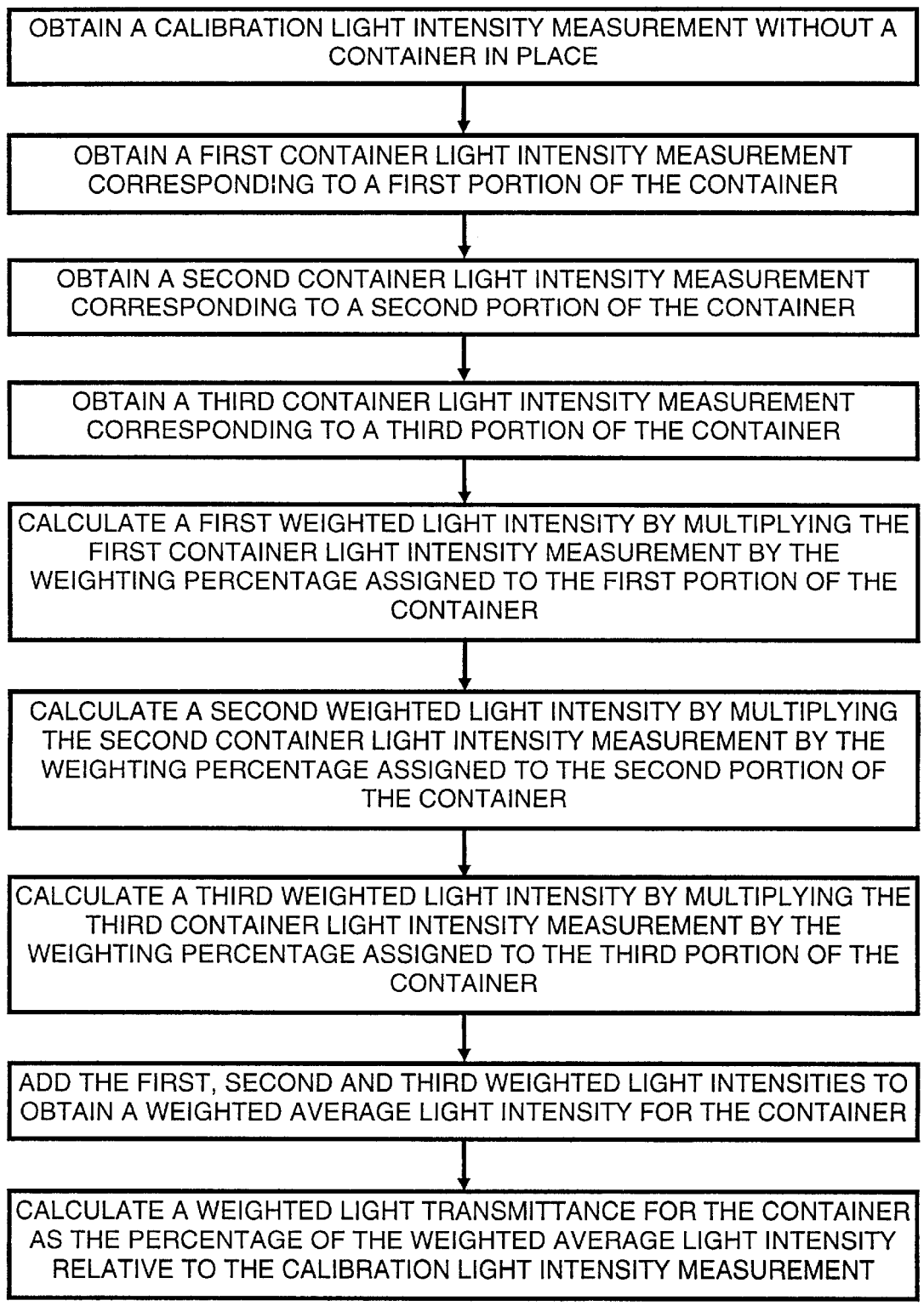
FIG. 10 is a flowchart illustrating another method for arriving at the weighted average light transmittance of a container.

As an alternative to averaging the percent light transmittance readings, the light intensity readings may first be averaged, in a manner as described above, and the percent light transmittance then calculated as follows:

$$\text{average percent transmittance} = \frac{100 \times WAILI}{DLI}$$

where WAILI=the weighted average indirect light intensity measured at a particular wavelength of light and DLI=the direct transmittance measured at the same wavelength of light during the calibration step. A graph, similar to that shown in FIGS. 2 and 3, may then be generated, showing the container's weighted average percent transmittance versus wavelength of light. The alternative procedure described above is illustrated in flowchart form in FIG. 10.

It is noted that the above procedure, in which the light transmittance of only three bottle points are acquired, is set forth by way of example only. In practice, it has been found that container light characteristics vary according to container design, secondary packaging, labeling, etc. Accordingly, the actual locations, number and relative weighting of container sampling points chosen will depend upon the characteristics of the particular container being evaluated. It is also noted that, in addition to the linearly separated sampling points described in the example above, sampling points may also be spaced circumferentially around the perimeter of the container at various locations.

Data Acquisition and Analysis

At each container measurement point, as described above, the percent light transmittance may be measured over a target range of light wavelengths, rather than at a single wavelength as in prior methods. This target range may be selected to closely correspond to the range of light wavelengths which most directly induces light struck flavor in beer. As previously described, the light struck flavor range of wavelengths has been found to include those wavelengths of light shorter than about 550 nm. It has also been found, however, that very short wavelengths, e.g. ultra violet light, are effectively blocked by even clear glass and plastic containers. It is, therefore, generally unnecessary to evaluate light transmittance for wavelengths less than about 400 nm, the approximate point at which the ultra violet range begins.

In order to provide overlap, the target range may be selected to be from about 380 nm to about 600 nm. Alternatively, the target range may be more narrowly selected to only include the critical range of from about 400 nm to about 550 nm.

Figure 2:
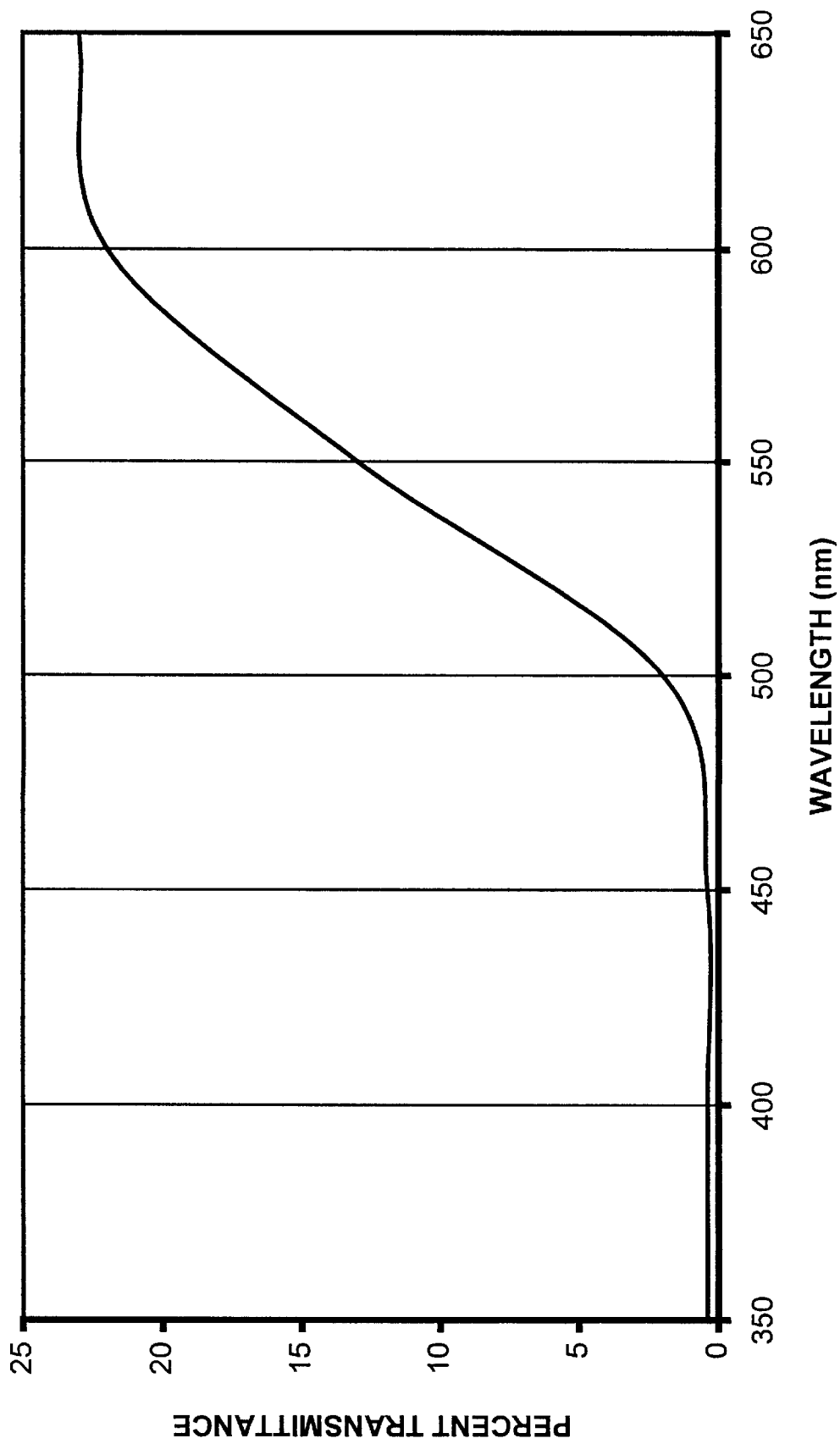
FIG. 2 is a graph illustrating percent transmittance versus wavelength of light in a relatively good container.
Figure 3:
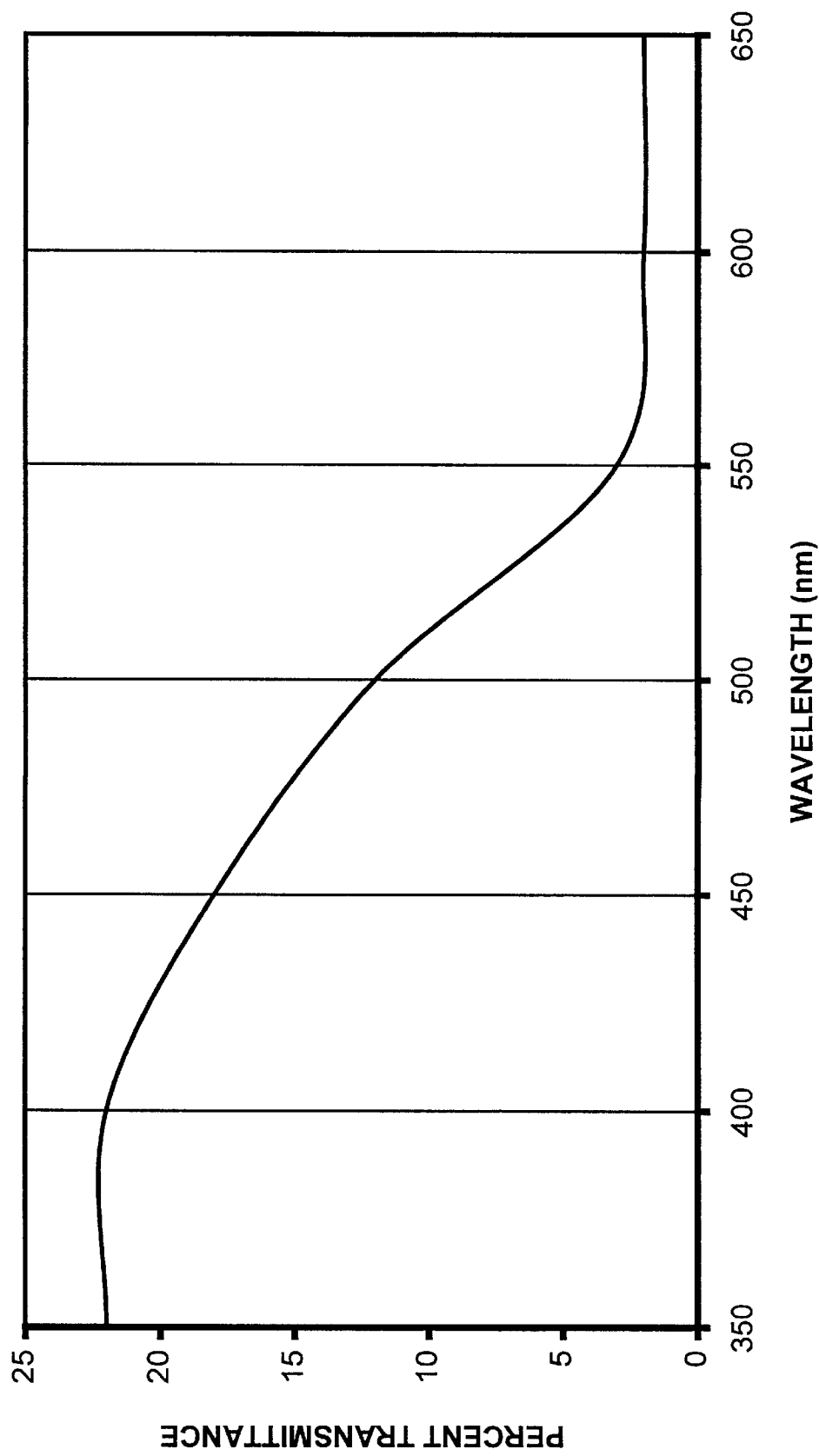
FIG. 3 is a graph illustrating percent transmittance versus wavelength of light in a container having relatively low transmittance at 550 nm, but relatively high transmittance over the remainder of the light struck flavor wavelength range.

For each measured point on a container, such as the bottle 140, the spectrophotometer may measure the light transmittance over the target range, as described above, for a number of generally equally spaced wavelengths. The spectrophotometer may, for example, measure the light transmittance at wavelength points which are spaced every 1 nm. Thus, over the 380 nm to 600 nm target range described above, 251 distinct light transmittance readings would be obtained. These points may then be used to generate graphs, such as the graphs shown in FIGS. 2 and 3, showing percent light transmittance versus wavelength of light.

Such graphs may be used to evaluate the ability of the material forming a particular container to prevent the formation of light struck flavor. Alternatively, an average of the light transmittance readings may be calculated and compared to an acceptable value in order to evaluate the ability of the material to guard against light struck flavor.

It is important to note that, in order to obtain reliable light transmittance readings over a target range, the light source 60 must be selected to provide adequate light over at least the target range selected. A xenon light source, as previously discussed, has been found to provide adequate light of a generally consistent intensity over the broad range of about 380 nm to 600 nm. As also previously discussed, other types of light sources, such as quartz halogen may also be used. It has been found, however, that a quartz halogen light source does not provide consistent light intensity at wavelengths shorter than about 450 nm. Accordingly, measurements made below 450 nm with a quartz halogen light source may be less sensitive.

The analytical method described above may be used with the container support apparatus 80 and associated methodology previously described. It may, however, also be used with any other type of data acquisition mechanism, such as the destructive test previously described.

The analytical method described above for measuring the transmittance of light is capable of more accurately detecting container samples that fail to adequately protect against light struck flavor. This analytical method would have detected, for example, that the sample analyzed in FIG. 3 is not capable of adequately protecting against light struck flavor. As previously discussed, the prior art method of analysis performed only at a light wavelength of 550 nm would indicate that the sample of FIG. 3 exhibits a transmittance of only about 3%, a relatively low transmittance. Accordingly, the prior art method of analysis would have erroneously indicated that the sample analyzed in FIG. 3 was acceptable.

The analytical method of the present invention, however, reveals that, even though the sample analyzed in FIG. 3 exhibits relatively low transmittance at a light wavelength of 550 nm, it nevertheless would not adequately prevent the formation of light struck flavor. Referring to FIG. 3, it can be seen that, although the sample analyzed has relatively low light transmittance at 550 nm, it exhibits relatively high transmittance over much of the target range of about 380 nm to 600 nm, as previously described. The present analytical method, as described above, would reveal a relatively high average light transmittance across the light struck flavor inducing range. Accordingly, the present analytical method would correctly indicate that the sample illustrated in FIG. 3 would not adequately prevent the development of light struck flavor whereas the prior art method would have failed to correctly predict the problem.

The software used to generate graphs, such as those shown in FIGS. 2 and 3 and to analyze the light transmittance data may be loaded on the computer 70 in a conventional manner. Such software is commercially available from Control Development Inc. as part of the previously referenced spectrophotometer card sold as part number CDIOSC/375-720/2.0.

As previously pointed out, light falling within the wavelength range of about 400 nm to about 550 nm generally induces light struck flavor in beer when it is packaged in translucent containers. Referring to FIG. 1, it can be seen, however, that not all wavelengths of light within this range equally impact light struck flavor. As can be appreciated from FIG. 1, light having wavelengths of between about 400 nm and about 450 nm induces a fairly constant light struck flavor rating of about 6.75. Between about 450 nm and 550 nm, however, the light struck flavor rating drops off dramatically. At 500 nm, for example, the light struck flavor rating has dropped to about 4.75 and at 550 nm, the light struck flavor rating is less than 1.0.

In order to more accurately measure the ability of a container to prevent the formation of light struck flavor, the individual light transmittance measurements, as described previously, may be weighted in order to account for this variation in light struck flavor inducement with respect to light wavelength. To perform such a weighting method, each light transmittance measured at a particular wavelength of light may be weighted according to the impact on light struck flavor induced by that particular wavelength of light. Thus, with the exemplary light struck flavor ratings set forth above, light having wavelengths from about 400 nm to about 450 nm might be weighted at 100 percent, since light in this wavelength range has the highest level of impact on light struck flavor. Each wavelength of light between about 450 nm and about 550 nm, on the other hand, may be weighted at a lower percentage according to the light struck flavor impact of that wavelength. Light at 550 nm, for example, might be weighted at about 70 percent since the light struck flavor rating at 550 nm (approximately 4.75) is about 70 percent of the light struck flavor rating of light wavelengths between about 400 nm and about 450 nm (approximately 6.75). Each wavelength within the range may be assigned a similar weighting percentage according to its relative tendency to induce light struck flavor.

When measuring light transmittance, in a manner as previously described, each light transmittance measurement obtained may be adjusted according to the weighting percentage of the wavelength point at the measurement is made. This adjustment may made before calculating the average of the light transmittance readings as previously described and/or before generating a graph, such as the graphs shown in FIGS. 2 and 3. In this manner, a more accurate indication may be obtained of the ability of a container to prevent the formation of light struck flavor.

It is noted that, although the above method has been described with specific reference to beer and light struck flavor in beer, many other types of beverages and food products are also packaged in translucent or semi-translucent containers and may be detrimentally affected by light. Accordingly, the analytical method described above is applicable to many types of products in addition to beer. The specific range of light wavelengths analyzed may be adjusted according to the particular sensitivities of the product which is to be placed in the container being tested.

Container Thickness Distribution Measurement & Calculation

The percent light transmittance procedure outlined above may also be used to calculate material distribution within a container as will now be described in detail. Percent light transmittance is influenced generally by two factors: the color and chemistry of the material forming the container; and the thickness of the material. In most containers, however, it has been found that the color and chemistry of the material forming the container is very consistent throughout the container. This is particularly true in the case of glass containers which are formed from large batches of generally well-mixed glass forming constituents.

Since the color and chemistry within a particular container are fairly consistent, most deviations in percent light transmittance from one area of a container to another are due solely to a difference in container wall thickness between the two areas.

The precise relationship between light transmittance and glass thickness depends on the specific color, glass chemistry of the glass used to make up a container and other variables, such as temperature. The following formula may be used to relate relative glass thickness to measured transmittance:

$$\frac{Th(2)}{Th(1)} = \frac{\ln\left(\frac{Tr(2)}{(1-R)^2}\right)}{\ln\left(\frac{Tr(1)}{(1-R)^2}\right)}$$

where $Th(1)$ is the thickness at a first location on the container, $Th(2)$ is the thickness at a second location on the container, $Tr(1)$ is the measured light transmittance at the first location (in decimal form) and $Tr(2)$ is the measured light transmittance at the second location (in decimal form). The value "R" is a measure of the reflectance of the glass and may be calculated as follows:

$$R = \left(\frac{n-1}{n+1}\right)^2$$

where "n" is the index of refraction for the particular glass. It can, thus, be appreciated that relative container wall material distribution may be determined by measuring percent light transmittance at desired locations and calculating the relative container wall thicknesses as described above.

An example of a relative glass thickness calculation for a typical amber glass container will now be described. In the case of a typical amber glass, for example, the index of refraction is about 1.5. Substituting this value into the previous equation yields an "R" value of:

$$R = \left(\frac{n-1}{n+1}\right)^2 = \left(\frac{1.5-1}{1.5+1}\right)^2 = \left(\frac{.5}{2.5}\right)^2 = 0.04$$

It is noted that the index of refraction for a particular glass will vary depending on the wavelength of light. This variance, however, is very small, particularly over the visible light spectrum and may, for purposes of the above equation assumed to be a constant value.

Continuing with the example, if a first transmittance $Tr(1)$ of 15% has been measured at the first location and a second transmittance $Tr(2)$ of 10% has been measured at the second location, then the thickness at the second location relative to the thickness at the first location may be calculated as follows:

$$\frac{Th(2)}{Th(1)} = \frac{\ln\left(\frac{Tr(2)}{(1-R)^2}\right)}{\ln\left(\frac{Tr(1)}{(1-R)^2}\right)} = \frac{\ln\left(\frac{.1}{(1-.04)^2}\right)}{\ln\left(\frac{.15}{(1-.04)^2}\right)} = 1.22$$

Accordingly, the thickness Th(2) at the second location is about 1.22 times the thickness Th(1) at the first location.

In addition, if the actual thickness of one measured area is known, then the actual thickness of all measured areas may readily be calculated as follows:

$$Th(2) = Th(1) * \frac{\ln\left(\frac{Tr(2)}{(1-R)^2}\right)}{\ln\left(\frac{Tr(1)}{(1-R)^2}\right)}$$

Accordingly, continuing with the example set forth previously, if the thickness Th(1) at the first location is ⅛ inch (0.125"), then the thickness Th(2) at the second location may be calculated as follows:

$$Th(2) = Th(1) * \frac{\ln\left(\frac{Tr(2)}{(1-R)^2}\right)}{\ln\left(\frac{Tr(1)}{(1-R)^2}\right)} = 0.125 * \frac{\ln\left(\frac{.1}{(1-.04)^2}\right)}{\ln\left(\frac{.15}{(1-.04)^2}\right)} = 0.153$$

Accordingly, the thickness at the second location is about 0.153 inches.

The formulas set forth above relating thickness to light transmittance are well recognized in the industry. See, for example, THE HANDBOOK OF GLASS MANUFACTURE—Volume II, compiled and edited by Fay V. Tooley and published by Books for Industry, Inc. and the Glass Industry Magazine Division of Magazines for Industry, Inc., 1974, Library of Congress No. 74-77520 at pages 961–975, which are hereby specifically incorporated by reference for all that is disclosed thereby.

It is noted that, for purposes of material thickness determinations, the transmittance measurements described above need only be made at a single wavelength of light. The method described above for measuring and calculating container material distribution is extremely efficient compared to prior methods which generally require cutting a container into many pieces and then physically measuring the thickness of the various pieces.

Glass Manufacturing Process Control

The methods described above for measuring the transmittance of light through a container wall may also be used to monitor the container manufacturing process in a manner as will now be described in detail. As previously described, the percent light transmitted through the wall of a container depends primarily upon two factors. The first factor is the thickness of the material forming the container in the location where the measurement is made, i.e., the thickness of material through which the light must pass. Obviously, relatively thicker material will allow relatively less light to be transmitted therethrough while relatively thinner material will allow relatively more light to be transmitted therethrough. The second factor is the physical composition of the material itself. Generally, for example, container material having a darker color will transmit less light than material having a relatively lighter color.

In the example of a glass container, the wall thickness of the container may be impacted by various factors in the glass making process. Physical wear, for example, of the molds which form the glass containers can affect the thickness of the glass in the completed container. Glass container wall thickness is also impacted by the temperature of the molds. Generally, cooler mold temperatures result in thicker container walls while relatively hotter mold temperatures will cause the walls to be thinner. During a typical glass forming process, the molds may also form hot or cool spots resulting in thinner or thicker areas on the container, respectively.

As previously described, the composition and color of finished glass containers depends upon the specific chemistry of the glass batch from which the containers were formed. The chemistry of the batch, in turn, can vary depending upon variations in the raw materials added to the batch. Glass batches tend to be fairly consistent throughout the batch at any given time. Also, because of the relatively large size of a batch, the composition of a batch tends to not vary significantly over small periods of time. Over longer periods of time, e.g. over a period of several days, however, the composition of a glass batch may show significant variation due to variation in the raw materials which have been added to the batch over time. This variation, or "drift" can cause undesirable changes in the composition of the resulting glass containers. Accordingly, it is desirable to monitor and adjust the batch composition over time.

A method for monitoring a container manufacturing process will now be described in detail. For exemplary purposes, the method will be described in conjunction with a glass making process, although it is to be understood that the method could alternatively be used with virtually any process for forming translucent containers.

Figure 12:
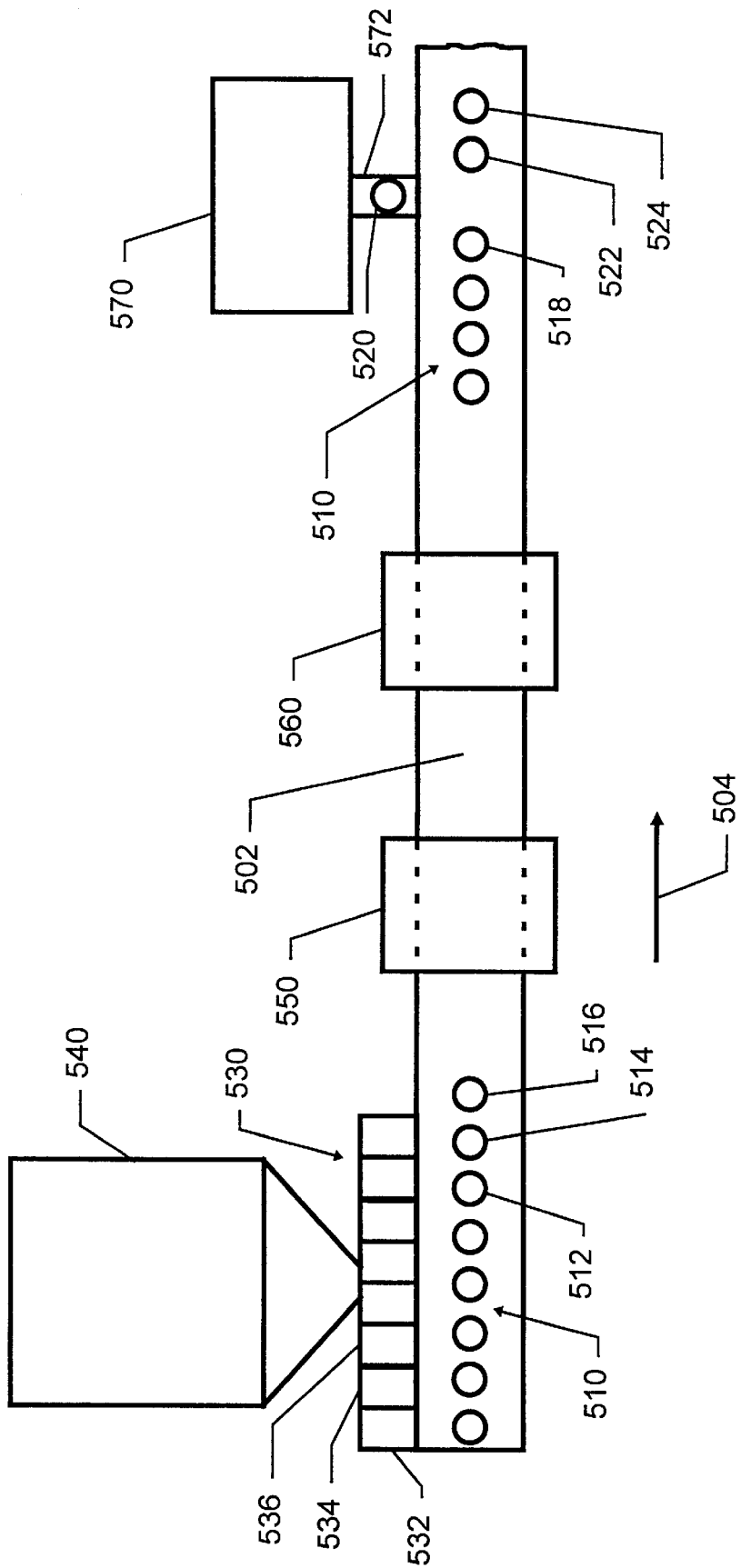
FIG. 12 is a schematic illustration of a container manufacturing line including a light transmittance measurement apparatus associated therewith.

FIG. 12 schematically illustrates a portion of a bottle production line 500. Bottle production line 500 includes a conveyor 502 which conveys a plurality of bottles 510, such as the individual bottles 512, 514, 516, 518, 520, 522, 524, in a conveying direction 504. The bottles 510 are formed in bottle mold assembly 530 which may include a plurality of individual bottle molds, such as the individual bottle molds 532, 534, 536. Molten glass is fed to the bottle mold assembly 530 from a batch furnace 540 in a conventional manner.

After being formed in the bottle mold assembly 530, the bottles 510 are transferred to the conveyor 502 in a conventional manner. Thereafter, the bottles 510 begin moving along the conveyor in the direction 504. After leaving the bottle mold area, the bottles 510 may be conveyed through a plurality of treatment devices, such as a hot coating hood 550 and an annealing oven 560, in a conventional manner.

Downstream of the annealing oven 560, a testing machine 570 may be located as shown. The testing machine 570 may include a conventional conveying apparatus 572 which is adapted to periodically remove one of the bottles 510, such as the illustrated bottle 520, from the conveyor 502 and into the interior of the testing machine 570. The testing machine 570 may be adapted to test selected bottles for various parameters such as bottle height, bottle diameter and the consistency of the diameter of the bottle. The testing machine 570 may, for example, be of the type commercially available from Inex, Inc. of Clearwater, Fla. and sold as a "Prolaser" bottle inspection device.

The light transmittance measurement apparatus probe 120, previously described, may, for example, be mounted on a moveable arm of the testing machine 570. In this manner, the moveable arm may cause the probe 120 to move into each of the sampled bottles in order to obtain a light transmittance reading. Acceptable bottles may then be returned to the container conveyor. In this manner, light transmittance readings may be performed automatically by the testing machine 570.

To accomplish the method for monitoring a container manufacturing process, a sample container 520 may first be removed from the container conveyor 502 at a location downstream of the annealing oven 560. The sample container 520 may then be analyzed for light transmittance by inserting the spectrometer probe 120 into the sample container 520 in a manner as previously described. Light transmittance may then be measured at a single point on the sample container 520. The probe 120 may, for example, be located adjacent the shoulder portion 148, FIG. 8, of the sample container 520 in order to measure the transmittance of light through this portion. The light transmittance may be measured over a range of light frequencies in a manner as also previously described.

As an alternative to measuring light transmittance at a single point, the container 520 may be rotated after the probe 120 is located adjacent the desired portion of the bottle. In this manner, a series of light transmittance readings may be obtained around the perimeter of the container at the height where the probe is located. The series of light transmittance readings may then be averaged or the highest light transmittance reading may be used.

After obtaining the light transmittance reading from the sample container, this light transmittance reading may be compared to a predetermined acceptable level of light transmittance for the shoulder area 148. If the measured light transmittance is within an acceptable range, then this generally indicates that no adjustment to the container manufacturing process is necessary. If, however, the measured light transmittance varies significantly from the acceptable range, i.e., a variant light transmittance measurement, then this indicates that the container manufacturing process is in need of adjustment.

Because light transmittance is impacted by both wall thickness and wall composition, as previously described, when a variant light transmittance reading is obtained, it is then further necessary to determine whether the wall thickness, the wall composition, or both are causing the variation in measured light transmittance. In order to make this determination, the wall thickness of the container may be measured at the point where the light transmittance was evaluated. The thickness measurement may be accomplished in a conventional manner, for example using calipers which are extended into the intact container. Alternatively, the portion of the container to be measured may first be cut from the bottle and then measured.

The measured thickness may then be compared to the acceptable thickness specification for that portion of the container. If the measured thickness is within specifications, then it can be assumed that a problem with the batch composition has caused the variation in light transmittance. In this case, the batch composition can be adjusted accordingly.

If, on the other hand, the glass thickness is not within specifications, then it can be assumed that the container thickness has contributed to the change in light transmittance. In order to determine whether the batch composition has also contributed to the variation in light transmittance, the following equation may be utilized:

$$C(sc) = \frac{\ln(T(sc))}{t(sc)}$$

where "T(sc)" is the measured light transmittance of the sample container in decimal form and "t(sc)" is the measured thickness of the sample container wall at the location where the light transmittance was measured. The result "C(sc)" is a value which is solely dependent upon the optical properties of the wall material composition and is independent of the thickness "t" of the material.

By applying this equation to the measured light transmittance and wall thickness of the sample container 520, the value "C(sc)" can be determined for the sample container and compared to a value "C(cc)" calculated for a control container. If the values of "C" for the sample container and the control container are substantially identical, then this indicates that the variance in measured light transmittance is being impacted solely by the change in material thickness since the substantially identical values of "C" between the control container and the sample container indicate that the control container and the sample container are formed from materials having substantially identical optical properties.

If, on the other hand, the values of "C" are not substantially identical, then this indicates that the variance in measured light transmittance is being impacted by a change in material composition in addition to change in material thickness between the sample container and the control container.

In the method described above, sample containers may be removed from the conveyor 502 and analyzed at a rate, for example, of about twenty containers per hour.

In practice, it is sometimes difficult to physically measure the thickness of a wall portion of a sample container. This is particularly true when a curved area, such as the shoulder area 148, FIG. 8, of a container is to be measured. Accordingly, as an alternative to physically measuring the wall thickness of the sample container, a "sample piece" may be manufactured in order to evaluate the optical properties value "C" of the batch. This value "C" may then be used to calculate the thickness of the wall portion of the actual sample container based upon the measured light transmittance through the wall portion of the sample container as will now be described in detail.

To manufacture the sample piece, a number, e.g., six, containers may be removed from the manufacturing line and crushed. The resulting crushed glass may then be melted and reformed into a disk. The disk may then be ground and polished until it has a uniform, known thickness of, e.g, 0.125 inches. The light transmittance may then be measured though the resulting ground and polished disk, or sample piece. After the light transmittance is measured, the value "C(sp)" may then be calculated according to the following equation:

$$C(sp) = \frac{\ln(T(sp))}{t(sp)}$$

where "T(sp)" is the measured light transmittance through the sample piece and "t(sp)" is the known thickness of the sample piece. As can be appreciated, the resulting sample piece value "C(sp)" will be indicative of the optical properties of the material from which the sample piece is formed.

The thickness of the sample container may then be calculated according to the following equation:

$$t(sc) = \frac{\ln(T(sc))}{C(sp)}$$

where "t(sc)" is the calculated thickness of the sample container, "T(sc)" is the measured light transmittance through the wall of the sample container and "C(sp)" is the optical property value calculated based upon the measured light transmittance and the known thickness of the sample piece.

In this manner, the thickness of the sample container wall portion may be calculated rather than measured. The calculated sample container thickness "t(sc)" may then be compared to the thickness specification for the container to determine if the container thickness is within specifications. The calculated sample piece optical properties value "C(sp)" may also be directly compared to the control container optical properties value "C(cc)" to determine whether the batch composition is in need of adjustment.

It is noted that, because the composition of a glass batch will change relatively slowly over time, the sample piece, as described above, need not be formed at precisely the same time that the sample container is formed. In practice, a sample piece may be formed, for example, about every twelve hours. Because any variation in the glass batch occurs very slowly, sample pieces formed at this time interval will generally exhibit a value "C(sp)" which is nearly identical to that currently exhibited by the container material batch.

The process described above is capable of detecting variations in both container thickness and container material composition at an early stage, before the variations become great enough to force rejection of the containers. In this manner, the process allows adjustments to be made so that containers will not have to be later rejected. Early detection of problems is particularly important with respect to batch composition variations because substantial time may be required to bring the batch back into proper balance. Accordingly, early indication of batch composition problems is essential to avoiding the necessity of rejecting containers.

Figure 11A:
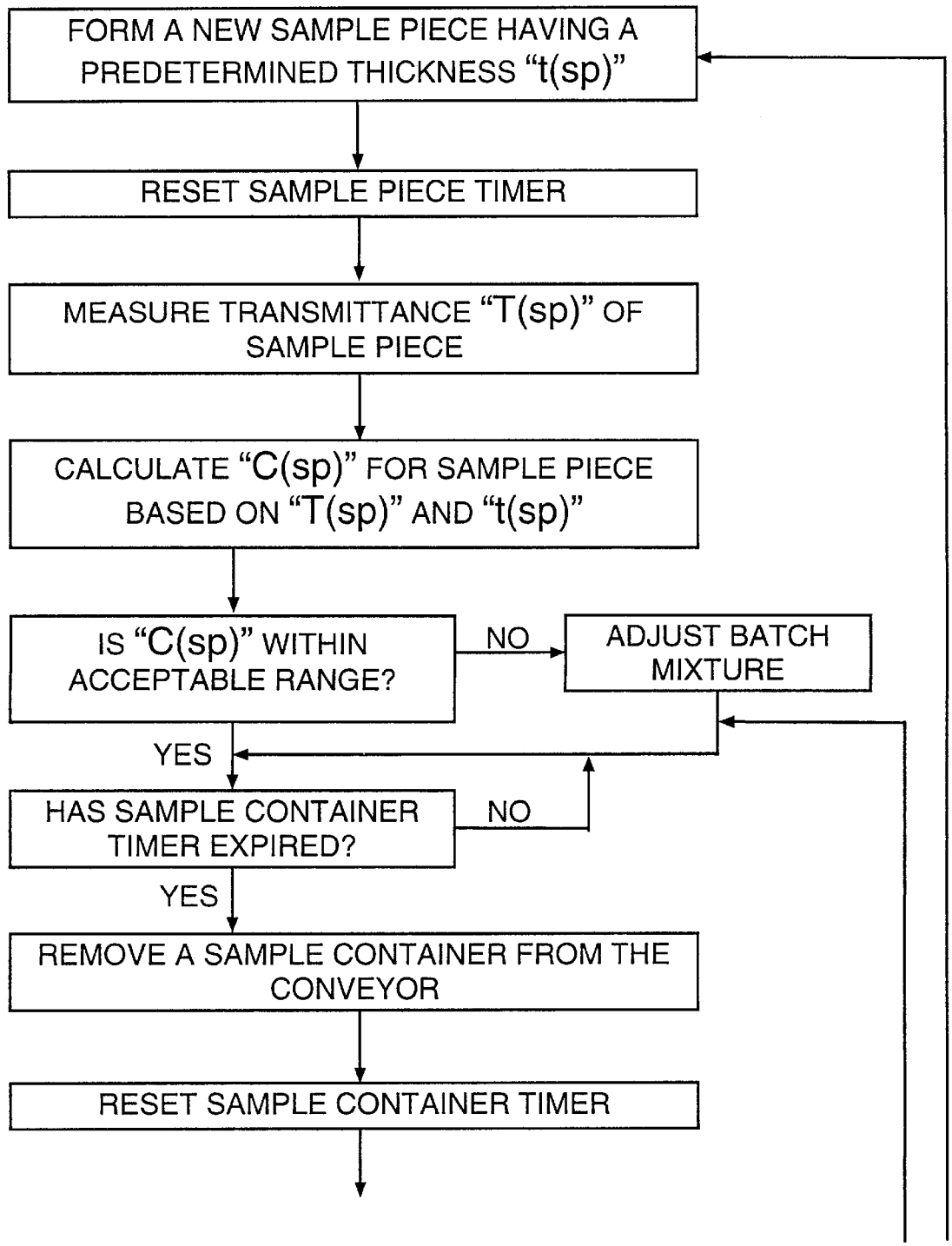
FIGS. 11A and 11B are a flowchart illustrating a method of controlling a container manufacturing process using measured light transmittance.
Figure 11B:
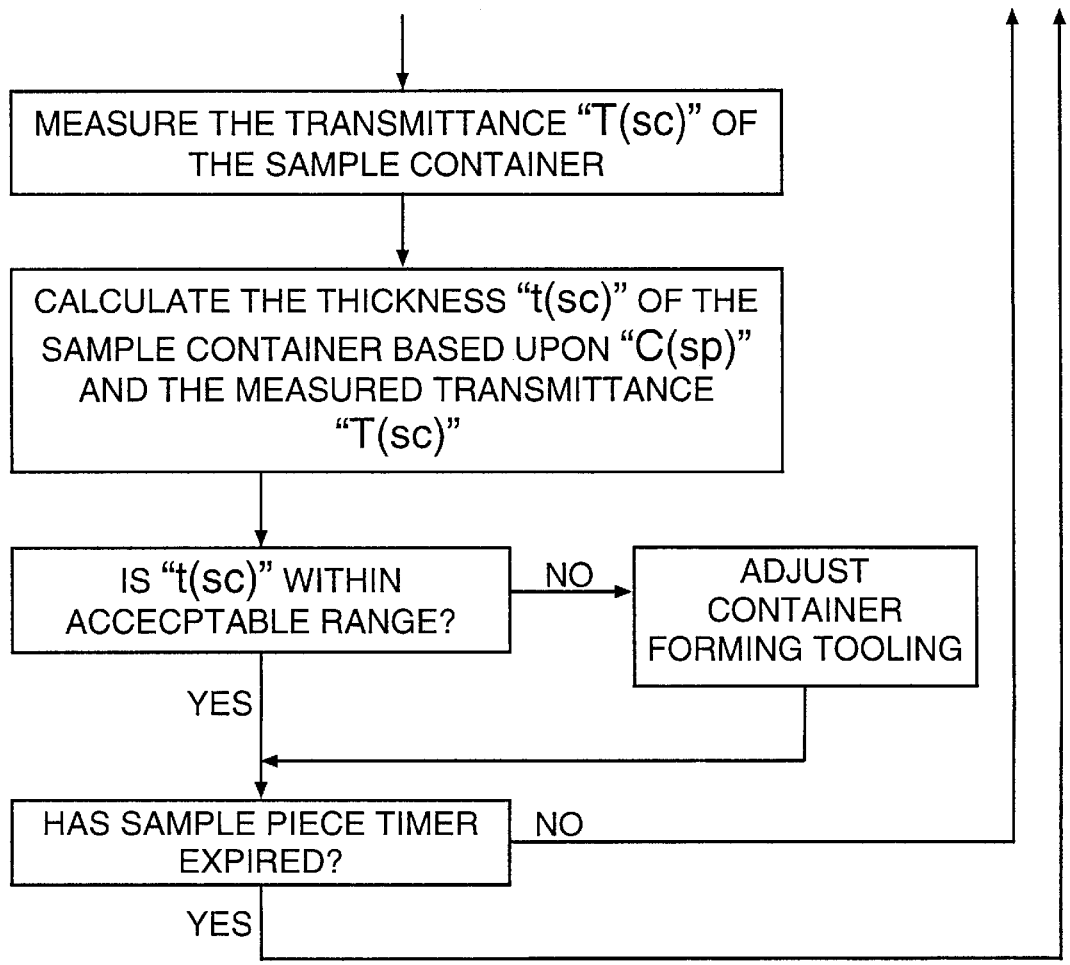

The process described above is illustrated in flow-chart form in FIGS. 11A and 11B.

It is noted that using the probe 120 and associated equipment previously described allows the container manufacturing process to be monitored without the need to destroy sampled containers. Use of this equipment also enables a high degree of automation to be used in the testing procedure.

It is further noted that, using the methodology previously described, the light transmittance of the sampled containers may be measured over a range of light frequencies in order to more accurately predict the ability of the containers to protect their contents against the adverse effects of light.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of monitoring a process for forming a plurality of translucent containers, comprising:
   providing in said process for forming a plurality of translucent containers:
   a. a supply of said material for forming the wall members of a plurality of containers;
   b. a container forming apparatus adapted to form said material into said plurality of containers;
   c. a conveying device adapted to convey said plurality of containers away from said container forming apparatus after the forming thereof;
   removing a statistical sample of containers from said plurality of containers conveyed on said conveying device;
   performing an analysis of said statistical sample of containers by:
   making a measurement of light transmittance through a first portion of a wall member of each of said statistical sample of containers; and
   making a comparison of each said measurement to a predetermined acceptable level of light transmittance;
   determining whether said process is in need of adjustment based upon the results of said analysis;
   wherein said first portion of said wall member of said sample container is an integral part of said sample container during said making a measurement of light transmittance.

2. The method of claim 1 further including:
   providing a light source;
   providing a spectrophotometer having a spectrophotometer probe associated therewith; and
   wherein said making a measurement of light transmittance comprises:
   a. positioning said sample container so that said spectrophotometer probe is at least partially located within said sample container and said first portion of said wall member of said sample container is located between said light source and said spectrophotometer probe;
   b. using said spectrophotometer to generate a first light intensity reading in response to said light supplied through said first portion.

3. The method of claim 2 wherein said making a measurement of light transmittance further comprises:
   supplying light from said light source directly onto said spectrophotometer probe;
   using said spectrophotometer to generate a direct light intensity reading in response to said directly supplied light;
   using said first light intensity reading and said direct light intensity reading to determine a percent transmittance of light through said first portion of said wall member of said sample container.

4. The method of claim 2 wherein said first light intensity reading comprises a set of light intensity readings from said spectrophotometer across a range of light frequencies.

5. The method of claim 3 wherein said direct light intensity reading comprises a set of light intensity readings from said spectrophotometer across a range of light frequencies.

6. The method of claim 4 wherein said range of light frequencies includes the range from about 400 nm to about 550 nm.

7. The method of claim 5 wherein said range of light frequencies includes the range from about 400 nm to about 550 nm.

8. The method of claim 1 and further including:
   determining the thickness of said first portion of said wall member of said sample container;
   using said measurement of light transmittance and said thickness of said first portion of said wall member of said sample container to determine at least one optical property of said material forming said wall member of said sample container.

9. The method of claim 8, wherein said least one optical property comprises the ability of said material forming said wall member of said sample container to block the transmission of light therethrough.

10. A method of monitoring a process for forming a plurality of translucent containers, comprising:
making a measurement of light transmittance through a first portion of a wall member of at least one sample container of said plurality of containers;
making a comparison of said measurement to a predetermined acceptable level of light transmittance;
determining whether said process is in need of adjustment based upon said comparison;
determining the thickness of said first portion of said wall member of said container;
using said measurement of light transmittance and said thickness of said first portion of said wall member of said sample container to determine at least one optical property of said material forming said wall member of said sample container;
wherein said light intensity reading comprises a set of light intensity readings across a range of light frequencies.

11. The method of claim 10 wherein said first portion of said wall member of said sample container is an integral part of said sample container during said step of making said measurement of light transmittance.

12. The method of claim 11 further including:
providing a light source;
providing a spectrophotometer having a spectrophotometer probe associated therewith; and
wherein said making a measurement of light transmittance comprises:
a. positioning said sample container so that said spectrophotometer probe is at least partially located within said sample container and said first portion of said wall member of said sample container is located between said light source and said spectrophotometer probe;
b. using said spectrophotometer to generate a first light intensity reading in response to said light supplied through said first portion.

13. The method of claim 12 wherein said making a measurement of light transmittance further comprises:
supplying light from said light source directly onto said spectrophotometer probe;
using said spectrophotometer to generate a direct light intensity reading in response to said directly supplied light;
using said first light intensity reading and said direct light intensity reading to determine a percent transmittance of light through said first portion of said wall member of said sample container.

14. The method of claim 13 wherein said direct light intensity reading comprises a set of light intensity readings from said spectrophotometer across a range of light frequencies.

15. The method of claim 14 wherein said direct light intensity reading comprises a set of light intensity readings from said spectrophotometer across a range including from about 400 nm to about 550 nm.

16. The method of claim 10 wherein said range of light frequencies includes the range from about 400 nm to about 550 nm.

17. The method of claim 11, wherein said least one optical property comprises the ability of said material forming said wall member of said sample container to block the transmission of light therethrough.

18. A method of measuring the transmittance of light through a wall of a container using a light source and a spectrophotometer having an associated probe comprising:
a. positioning said container so that said spectrophotometer probe is at least partially located within said container and a first portion of said wall of said container is located between said light source and said probe;
b. supplying light from said light source onto said spectrophotometer probe through said first portion;
c. using said spectrophotometer to generate at least a first light intensity reading in response to said light supplied through said first portion of said wall of said container; and
d. using said at least a first light intensity reading to determine a percent transmittance of light through said wall of said container.

19. The method of claim 18 wherein said at least a first light intensity reading comprises a first set of light intensity readings from said spectrophotometer across a range of light frequencies.

20. The method of claim 19 wherein said range of light frequencies includes the range from about 400 nm to about 550 nm.

21. The method of claim 18 and further including:
a. repositioning said container so that a second portion of said wall of said container is located between said light source and said probe;
b. supplying light from said light source onto said spectrophotometer probe through said second portion of said container;
c. using said spectrophotometer to generate at least a second light intensity reading in response to said light supplied through said second portion of said container; and
d. using said at least a first and at least a second light intensity readings to determine a percent transmittance of light through said wall of said container.

22. The method of claim 21 wherein said at least a second light intensity reading comprises a second set of light intensity readings from said spectrophotometer across a range of light frequencies.

23. The method of claim 22 wherein said range of light frequencies includes the range from about 400 nm to about 550 nm.

24. The method of claim 21 including the further step of averaging said at least a first and at least a second light intensity readings.

25. The method of claim 21 and further including:
  a. assigning a first weighting percentage to said first portion of said wall of said container;
  b. assigning a second weighting percentage to said second portion of said wall of said container;
  c. calculating a weighted average of said at least a first and at least a second light intensity readings according to said first and second weighting percentages.

26. The method of claim 25 wherein said first and second weighting percentages are assigned according to the expected exposure to light of the first and second portions of said wall of said container, respectively.

27. The method of claim 19 and further including:
  a. assigning a weighting percentage to each light frequency within said range of light frequencies; and
  b. using said assigned weighting percentages to determine said percent transmittance of light.

* * * * *